United States Patent
Reenan et al.

(10) Patent No.: US 7,118,873 B2
(45) Date of Patent: Oct. 10, 2006

(54) POLYNUCLEOTIDES ENCODING CELLULAR TRANSPORTERS AND METHODS OF USE THEREOF

(75) Inventors: Robert A. Reenan, West Hartford, CT (US); Blanka Rogina, West Hartford, CT (US); Stephen L. Helfand, Orange, CT (US)

(73) Assignee: The University of Connecticut, Storrs, CT (US)

( * ) Notice: Subject to any disclaimer, the term of this patent is extended or adjusted under 35 U.S.C. 154(b) by 324 days.

(21) Appl. No.: 10/017,479

(22) Filed: Dec. 12, 2001

(65) Prior Publication Data

US 2003/0104399 A1    Jun. 5, 2003

Related U.S. Application Data

(60) Provisional application No. 60/255,013, filed on Dec. 12, 2000.

(51) Int. Cl.
G01N 33/53 (2006.01)
G01N 33/567 (2006.01)
C12N 15/63 (2006.01)

(52) U.S. Cl. .................... 435/7.1; 435/7.2; 435/7.21; 435/252.3; 436/501; 530/350

(58) Field of Classification Search ................ 530/350; 424/9.1; 436/501
See application file for complete search history.

(56) References Cited

U.S. PATENT DOCUMENTS

| | | | |
|---|---|---|---|
| 4,458,066 A | 7/1984 | Caruthers et al. ............. 536/27 |
| 4,695,590 A | 9/1987 | Lippman .................... 514/724 |
| 4,833,128 A | 5/1989 | Solomon et al. .............. 514/23 |
| 4,873,191 A | 10/1989 | Wagner et al. ........... 435/172.3 |
| 4,946,778 A | 8/1990 | Ladner et al. ............. 435/69.6 |
| 5,093,246 A | 3/1992 | Cech et al. .................... 435/91 |
| 5,223,409 A | 6/1993 | Ladner et al. ............. 435/69.7 |
| 5,238,963 A | 8/1993 | Cerami et al. .............. 514/632 |
| 5,270,163 A | 12/1993 | Gold et al. ..................... 435/6 |
| 5,270,170 A | 12/1993 | Schatz et al. .............. 435/7.37 |
| 5,283,173 A | 2/1994 | Fields et al. .................... 435/6 |
| 5,371,089 A | 12/1994 | Rattan ........................ 514/261 |
| 5,543,405 A | 8/1996 | Keown et al. ............... 514/188 |
| 5,597,797 A | 1/1997 | Clark ........................... 514/12 |
| 5,614,407 A | 3/1997 | Rattan ........................ 435/375 |
| 5,681,744 A | 10/1997 | Greenstein ............... 435/320.1 |
| 5,702,902 A | 12/1997 | Tartaglia ........................ 435/6 |
| 5,741,666 A | 4/1998 | Tartaglia .................... 435/69.1 |
| 5,744,300 A | 4/1998 | Linskens et al. |
| 5,744,477 A | 4/1998 | Cincotta et al. ............. 514/288 |
| 5,760,047 A | 6/1998 | Cincotta et al. ............. 514/288 |
| 5,762,936 A | 6/1998 | Ronzio et al. ........... 424/195.1 |
| 5,817,782 A | 10/1998 | Jazwinski .................. 536/23.1 |
| 5,859,183 A | 1/1999 | de Lange et al. ........... 530/300 |
| 5,859,308 A | 1/1999 | Mirochnitchenko et al. ... 800/2 |
| 5,861,485 A | 1/1999 | Tartaglia ..................... 530/351 |
| 5,874,210 A | 2/1999 | Guarente et al. ............... 435/4 |
| 5,910,490 A | 6/1999 | Moczar et al. ................. 514/54 |
| 5,912,227 A | 6/1999 | Croom, Jr. et al. ........... 514/12 |
| 5,914,326 A | 6/1999 | McCarty et al. ............ 514/188 |
| 5,919,618 A | 7/1999 | Guarente et al. ............... 435/6 |
| 6,013,622 A | 1/2000 | Bruno et al. ................... 514/2 |
| 6,020,166 A | 2/2000 | De Lange et al. ......... 435/69.1 |
| 6,022,709 A | 2/2000 | de Lange et al. .......... 435/69.1 |
| 6,040,310 A | 3/2000 | Dow et al. .................. 514/258 |
| 6,043,346 A | 3/2000 | Kleyn et al. ............. 530/387.9 |
| 6,048,837 A | 4/2000 | Friedman et al. ............... 514/2 |
| 6,048,900 A | 4/2000 | Connell et al. ............. 514/663 |
| 6,054,590 A | 4/2000 | Poindexter et al. ...... 548/311.1 |
| 6,057,109 A | 5/2000 | Tartaglia ........................ 435/6 |
| 6,086,878 A | 7/2000 | Adalsteinsson et al. .. 424/157.1 |
| 6,096,745 A | 8/2000 | Poindexter et al. ..... 514/252.05 |
| 6,096,885 A | 8/2000 | Dezube et al. .............. 540/527 |
| 6,100,048 A | 8/2000 | Cone et al. ................. 435/7.21 |
| 6,100,085 A * | 8/2000 | Amara et al. ............. 435/317.1 |
| 6,121,017 A | 9/2000 | Tartaglia .................... 435/69.1 |
| 6,127,424 A | 10/2000 | Martin et al. ............... 514/646 |
| 6,136,367 A | 10/2000 | Hoie .......................... 426/634 |
| 6,140,354 A | 10/2000 | Dax et al. ................... 514/357 |
| 6,225,120 B1 | 5/2001 | Ruvkun et al. |
| 6,287,782 B1 | 9/2001 | Tartaglia et al. ............. 435/7.1 |
| 6,303,768 B1 | 10/2001 | Lin et al. ................... 536/23.4 |
| 2001/0016332 A1 | 8/2001 | Ruvkun et al. |
| 2001/0029617 A1 | 10/2001 | Ruvkun et al. |
| 2002/0019028 A1 | 2/2002 | Chaturvedi et al. |

(Continued)

FOREIGN PATENT DOCUMENTS

EP        0 475 553 A2    3/1992

(Continued)

OTHER PUBLICATIONS

Chen et al. (1999), "Molecular and functional analysis of SDCT2, a novel rate sodium-dependent dicarboxylate transporter," J. Clin. Invest. 103: 1159-1168.*

(Continued)

Primary Examiner—Christine J. Saoud
Assistant Examiner—Jon M Lockard
(74) Attorney, Agent, or Firm—McCarter & English, LLP

(57) ABSTRACT

This disclosure encompasses the Indy gene, polypeptides encoded by the Indy gene and fragments thereof. This disclosure also encompasses homologs of the Indy gene both from *Drosophila* and other organisms. In addition, this disclosure encompasses the use of Indy polynucleotides, INDY proteins and polypeptides, antibodies to the INDY protein, antagonists that inhibit Indy activity or expression, and agonists that increase Indy activity or expression, in the diagnosis or treatment of body weight disorders or longevity in humans and animals.

21 Claims, 22 Drawing Sheets

U.S. PATENT DOCUMENTS

2002/0120008 A1   8/2002   Benzer et al.

FOREIGN PATENT DOCUMENTS

| WO | WO 92/06204 | 4/1992 |
|---|---|---|
| WO | WO 97/41242 | 6/1997 |
| WO | WO 99/10482 | 3/1999 |
| WO | WO 99/64458 | 12/1999 |
| WO | WO 00/11952 | 3/2000 |
| WO | WO 00/37938 | 6/2000 |
| WO | WO 01/12851 A2 | 2/2001 |
| WO | WO 01/35096 A2 | 5/2001 |

OTHER PUBLICATIONS

Pajor (1996), "Molecular cloning and functional expression of a sodium-dicarboxylate cotransporter from human kidney," Am. J. Physiol. 270: F642-F648.*

Pajor, A.M. (1999). Sodium-coupled transporters for Krebs cycle intermediates. Annu. Rev. Physiol. 61:663-82; See p. 664.*

Bitter, et al., "Expression and Secretion Vectors for Yeast", in Methods In Enzymology, vol. 153, pp. 516-545 (1987).

Logan, et al., "Adenovirus tripartite leader sequence enhances translation of mRNAs late after infection", in Proc. Natl. Acad. Sci., vol. 81, pp. 3655-3659 (1984).

Maitland, et al., "Biochemical Transformation of Mouse Cells by Fragments of Herpes Simplex Virus DNA", Cold Spring Harbor Laboratory, in Cell, vol. 11, pp. 233-241 (1977).

Szybalska, et al., "Genetics of Human Cell Lines, IV. DNA-Mediated Heritable Transformation of a Biochemical Trait", McArdle Memorial Laboratory, University of Wisconsin, pp. 2026-2034 (1962).

Lowy, et al., "Isolation of Transforming DNA: Cloning the Hamster aprt Gene", in Cell, vol. 22, pp. 817-823 (1980).

Saiki, et al., "Enzymatic Amplification of B-Globin Genomic Sequences and Restriction Site Analysis for Diagnosis of Sicle Cell Anemia", in Science, vol. 230, pp. 1350-1354 (1985).

Saiki, et al., "Primer-Directed Enzymatic Amplification of DNA with a Thermostable DNA Polymerase", in Science, vol. 239, pp. 487-491 (1988).

Narang, et al., "Improved Phosphotriester Method for the Synthesis of Gene Fragments", pp. 90-99.

Brown, et al., "Chemical Synthesis and Cloning of a Tyrosine tRNA Gene", in Methods In Enzymology, vol. 68, pp. 109-151.

Beaucage, et al., "Deoxynucleoside Phosphoramidites—A New Class Of Key Intermediates For Deoxypolynucleotide Synthesis", in Tetrahedron Letters, vol. 22, pp. 1859-1862 (1981).

Matteucci, et al., "Synthesis of Deoxyoligonucleotides on a Polymer Support", in American Chemical Society, vol. 103, No. 11, 1981.

Altschul, et al., "Basic Local Alignment Search Tool", J. Mol. Biol. (1990) 215, pp. 403-410.

Cunningham, et al., "High-Resolution Epitope Mapping of hGH-Receptor Interacations by Alanine-Scanning Mutagenis", in Science, Vo. 244, pp. 1081-1085 (1989).

Bass, et al., "A systematic mutational analysis of hormone-binding determinants in the human growth hormone receptor", Proc. Natl. Acad. Sci. USA, vol. 88, pp. 4498-4502 (1991).

De Vos, et al., "Human Growth Hormone and Extracellular Domain of Its Receptor: Crystal Structure of the Complex", in Science, vol. 255, pp. 306-312 (1992).

Smith, et al., "Human Interleukin 4—The Solution Structure of a Four-helix Bundle Protein", Inorganic Chemistry Laboratory and Department of Biochemistry, University of Oxfoed, pp. 899-904 (1992).

Wlodaver, et al., "Crystal structure of human recombinant interleukin—4 at 2.25 A resolution", Macromolucar Structure Laboratory, NCI-Frederick Cancer Research and Development Center, pp. 59-64 (1992).

Reidhaar-Olson, et al., "Combinatorial Cassette Mutagenesis as a Probe of the Informational Content of Protein Sequences", in Science, vol. 241, pp. 53-57 (1988).

Kohl, et al., "Selective Inhibition of ras-Dependent Transformation by a Farnesyltransferase Inhibitor", in Science, vol. 260, pp. 1934-1937 (1993).

Bowie, et al., "Identifying determinants of folding and activit for a protein of unknown structure", Proc. Natl. Acad. Sci. USA, vol. 86, pp. 2152-2156 (1989).

Derbyshire, et al., "A simple and efficient procedure for saturation mutagenesis using mixed oligodeoxynucleotides", Department of Molecular Biophysics and Biochemistry, Yale University, pp. 145-152 (1986).

Ner, et al., "Laboratory Methods—A Simple and Efficient Procedure for Generating Random Point Mutations and for Codon Replacements Using Mixed Oligodeoxynucleotides", DNA, vol. 7, No. 2, pp. 127-134 (1988).

Jones, et al., "Replacing the complementarity-determining regions in a human antibody with those from a mouse", Nature vol. 321, pp. 522-525 (1986).

Karjalainen, et al., "An unusual type of V-J joining diversifies the primary repertoire of mouse 1 light chains", in Nature, vol. 314, pp. 544-546 (1985).

Singer, et al., "Optimal Humanization of 1B4, an Anti-CD18 Murine Monoclonal Antibody, Is Achieved by Correct Choice of Human V-Region Framework Sequences", The Journal of Immunology, vol. 150, pp. 2844-2857 (1993).

Lam et al., "Rational Design of Potent, Bioavailable, Nonpeptide Cyclic Ureas as HIV Protease Inhibitors", in Science, vol. 263, pp. 380-383 (1994).

Simon, et al., "Peptoids: A modular approach to drug discovery", Proc. Natl. Acad. Sci. USA 89, pp. 9367-9371 (1992).

Scott, et al., "Searching for Peptide Ligands with an Epitope Library", in Science, vol. 249, pp. 386-390 (1990).

Devlin, et al., "Random Peptid Libraries: A Source of Specific Protein Binding Molecules", Department of Molecular Biology, Cetus Corporation, pp. 404-405.

Edgington, Stephen M; "Shape Space", Bio/Technology vol. 11, pp. 285-289 (1993).

DeWitt, et al., "Diversomers: An approach to nonpeptide, nonoligomeric chemical diversity", Proc. Natl. Acad. Sci. USA, vol. 90, pp. 69j09-6913 (1993).

Erb, et al., "Recursive deconvolution of combinatorial chemical libraries", Proc. Nat. Acad. Sci. USA, vol. 91, 11422-11426 (1994).

Zuckerman, et al., "Discovery of Nanomolar Ligands for 7-Transmembrane G-Protein-Coupled Receptors from a Diverse N-(Substituted)glycine Peptoid Library", Journal of Medicinal Chemistry, vol. 37, No. 17, pp. 2678-2685 (1994).

Gallop, et al., Applications of Combinatorial Technologies to Drug Discovery. 1. Background and Peptide Combinatorial Libraries:, Journal of Medicinal Chemistry, vol. 37, No. 9, pp. 1233-1250 (1994).

Cho, et al., "An Unnatural Biopolymer", in Science, vol. 261, pp. 1303-1307 (1993).

Fodor, et al. "Multiplexed biochemical assays with biological chips", Nature vol. 364 pp. 555-556, Aug. 5, 1993.

Cull et al. "Screening for receptor ligands using large libraries of peptides linked to the C terminus of the lac repressor", Proc. Natl. Acad. Sci. USA, vol. 89, pp. 1865-1869, Mar. 1992.

Cwirla et al. "Peptides on phage: A vast library of peptides for identifying ligands"., Proc. Natl. Acad. Sci. USA, vol. 87, pp. 6378-6382, Aug. 1990.

Houghten, et al. "The Use of Synthetic Peptide Combinatorial Libraries for the Identification of Bioactive Peptides". BioFeature vol. 13. No. 3 (1993).

Lam et al. "A new type of synthetic peptide library for identifying ligand-binding activity". Nature. vol. 354 pp. 82-83 Nov. 7, 1991.

Gordon, "Transgenic Animals". International Review of Cytology, vol. 115 pp. 171-229 (1989).

Fire et al. "Potent and specific genetic interference by double-stranded RNA in Caenorhabditis elegans". Nature. vol. 391. pp. 806-811. Feb. 19, 1998.

Boynton, et al. "latheo, a New Gene Involved in Associative Learing and Memory in *Drosphila melanogaster*, Identified from P Element Mutagenesis". Genetics 131. pp. 655-672 (Jul. 1992).

Coady, et al. "Expression of Mammalian Renal Transporters in *Xenopus laevis* Oocytes". Archives of Biochemistry and Biophysics. vol. 283, No. 1 pp. 130-134 (Nov. 1, 1990).

Pajor, et al. "Cloning and Functional Expression of a Mammalian Na+/Nucleoside Contransporter". The Journal of Biological Chemistry. vol. 267. No. 6 pp. 3357-3560, (1992).

Pajor, Ana M. "Sequence and Functional Characterization of a Renal Sodium/Dicarboxylate Contransporter". The Journal of Biological Chemistry. vol. 270, No. 11, pp. 5779-5785 (1995).

Pajor, et al. "Sodium and Lithium Interactions with the Na+/Dicarboxylate Contransporter". The Journal of Biological Chemistry. vol. 273. No. 30. pp. 18923-18929 (1998).

Chen et al. "Characterization of a Rat Na+-Dicarboxylate Contransporter" The Journal of Biological Chemistry. vol. 278. No. 33. pp. 20972-20981 (1998).

Baum "Combinatorial Approches Provide Fresh Leads for Medicinal Chemistry" Science/Technology pp. 20-27(1994).

Averill "Novel Copper Nitrosyl Complexes: Contributions to the Understanding of Dissimilatory, Copper-Containing Nitrite Reductases" Highlights No. 20, pp. 2057-5064 (1994).

Coady, et al. "Expression of Mammalian Renal Transporters in *Xenopus laevis* Oocytes". Archives of Biochemistry and Biophysics. vol. 283, No. 1. pp. 130-134. (1990).

Tsai, et al. "In Vitro Selection of RNA Epitopes Using Autoimmune Patient Serum". The Journal of Immunology. vol. 150. No. 3. pp. 1137-1145. Feb. 1, 1993.

Marasco, et al. "Design, intracellular expression, and activity of a human anti-human immunodeficiency virus typ 1 gp 120 signle -chain antibody". Proc. Natl. Acad. Sci. USA vol. 90. pp. 7889-7893 ( Aug. 1993).

Chien, et al. "The two-hybrid system: A method to identify and clone genes for proteins that interact with a protein of interest" Proc. Natl. Acad. Sci. USA. vol. 88. pp. 9578-9582. (Nov. 1991).

Holtzman, et al. "Synthetic-lethal Interactions Identify Two Novel Genes, SLA1 and SLA2, That Control Membrane Cytoskeleton Assembly in *Saccharomyces cerevisiae*". The Journal of Cell Biology. vol. 122. No. 3. pp. 635-644. (Aug. 1993).

Putten, et al. "Efficient insertion of genes into the mouse germ line via retroviral vectors". Proc. Natl. Acad. Sci. USA. vol. 82. pp. 6148-6152 (Sep. 1985).

Thompson, et al. "Germ Line Transmission and Expression of a Corrected HPRT Gene Produced by Gene Targeting in Embryonic Stem Cells". Cell. vol. 56. pp. 313-321. Jan. 27, 1989.

Lo "Transformation by Iontophoretic Microinjection of DNA: Multiple Integrations Without Tandem Insertions". Molecular and Cellular Biology. pp. 1803-1814. (Oct. 1983).

Lavitrano, et al. "Sperm Cells as Vectors for Introducing Foreign DNA into Eggs: Genetic Transformation of Mice". Cell. vol. 57. pp. 717-723. (Jun. 2, 1989).

Pajor., "Sodium-Coupled Transporters for Krebs Cycle Intermediates". Annu. Rev. Physiol, 1999. 61:663-682.

Pajor et al., "Molecular cloning, chromosomal organization, and functional characterization of a sodium-dicarboxylate cotransporter from mouse kidney". Am J. Physiol Renal Physiol 279: F482-F490, 2000.

Sekine, et al. "Cloning, Functional Characterization, and localization of a rat renal Na+-dicarboxylate transporter". The American Physiological Society. pp. F298-F305 (1998).

Felici, et al. "Selection of Antibody Ligands from a Large Library of Oligopeptides Expressed on a Multivalent Exposition Vector". J. Mol. biol. pp. 301-310. (1991).

Tsai, et al. "In vitro selection of an RNA epitope immunologically cross-reactive witha peptide". Proc. Natl. Acad. Sci. USA. vol. 89. pp. 8864-8868 (Oct. 1992).

Harlow, "Screening Monoclonal Antibodies". Antibodies: A Labortory Manual. Chapter 6. pp. 174-189.

Fly Base No: CG3979 , AF217399.

Baum, Rudy M. "Combinatorial Approcaches Provide Fresh Leads for Medicinal Chemistry" Science/Technology. pp. 20-26 (Feb. 7, 1994).

Barbas, et al. Combinatorial Immunoglobulin Libraries on the Surface of Phage (Phabs): Rapid Selection of Antigen-Specific Fabs. METHODS vol. 2. pp. 119-124 (1991).

Carell, et al. "A Novel Procedure for the Synthesis of Libraries Containing Small Organic Molecules". COMMUNICATIONS. pp. 2059-2061 (1994).

Carell, et al. "A Solution-Phase Screening Procedure for Isolation of Active Compounds from a Library of Molecules". COMMUNICATIONS. pp. 2061-2064. (1994).

Coligan, et al. "Current Protocols in Immunology". Green Publishing. (1992).

Chen, et al. Accession No: AF058714.
Schmid, et al. Accession No: AF217399.
Adams, et al. Accession No: AE003728.
Pajor Accession No: U26209.
Kekuda et al. Accession No: AF081825.
Pajor Accession No: U12186.
Pajor et al. Accession No: AF201903.
Adams et al. Accession No: AE003519.

Blake et al., "A Molecular Marker Confirms That the Rate of Adult Maturation Is Largely Independent of the Rate of Pre-Adult Development in *Drosophila melanogaster*", Dev Genetics 18:125-130 (1996).

Blake et al., "Changes in gene expression during post-eclosional development in the olfactory system of *Drosophila melanogaster*", Mech. Dev. 52:179-185 (1995).

Clancy et al., "Dietary Restriction in Long-Lived Dwarf Flies", Science 296:319 (2002).

Clancy et al., "Extension of Life-Span by Loss of CHICO, a *Drosophila* Insulin Receptor Substrate Protein", Science 292:104-106 (2001).

DePinho, "The age of cancer", Nature 408:248-254 (2000).

Finkel et al., "Oxidants, oxidative stress and the biology of ageing", Nature 408:239-247 (2000).

Girard et al., "Molecular cloning and functional analysis of SUT-1, a sulfate transporter from human high endothelial venules", PNAS 96:12772-12777 (1999).

Guarente et al., "Genetic pathways that regulate ageing in model organisms", Nature 408:255-262 (2000).

Hayflick, "The future of ageing", Nature 408:267-269 (2000).

Helfand et al., "The expression of a reporter protein, β-galactosidase, is preserved during maturation and aging in some cells of the adult *Drosophila melanogaster*", Mech. Dev. 55:45-51 (1996).

Helfand et al., "Regulation of Gene Expression During Aging", Res. And Prob. In Cell Diff. 29:67-80 (2000).

Helfand et al., "Temporal Patterns of Gene Expression in the Antenna of the Adult *Drosophila melanogaster*", Genetics 140:549-555 (1995).

Helfand, "Single Gene Mutants that Confer Longevity in Drosophila", Abstract Grant No. 5R01AG016667-04, CRISP Database, May 21, 2002.

Kari et al., "Roles for Insulin-Like Growth Factor-1 in Mediating the Anti-Carcinogenic Effects of Caloric Restriction", J. Nutr. Health & Aging 3:92-101 (1999).

Kirkwood et al., "Why do we age?", Nature 408:233-238 (2000).

Knauf et al., "Functional characterization and immunolocalization of the transporter encoded by the life-extending gene Indy", PNAS 99:14315-14319 (2002).

Martin et al., "Lessons from human progeroid syndromes", Nature 408:263-266 (2000).

NCBI Accession No. AAF49226, Adams et al., Mar. 21, 2000.
NCBI Accession Nos. AE003519 AE002602, Adams et al., Sequence Listing, Mar. 21, 2000.
NCBI BLASTP 2.2.3, Altschul et al., Sequence Listing, Apr. 24, 2002.
NCBI Accession No. NP_036582, Girard et al., PRI Dec. 19, 2001.
NCBI Accession No. BAB15477, Kawakami et al., Aug. 29, 2000.
NCBI Accession No. CAC18857, Lloyd, Apr. 4, 2001.
NCBI Accession No. BAB71262, Oshima et al., Oct. 24, 2001.
NCBI Accession No. NP_003975, Pajor et al., PRI Nov. 1, 2000.
NCBI Accession No. NP_073740, Wang et al., PRI Oct. 25, 2001.
NCBI Accession No. XP_017841, NCBI Annotation Project, May 9, 2002.
NCBI Accession No. XP_031387, NCBI Annotation Project, May 9, 2002.

NCBI Accession No. XP_091606, NCBI Annotation Project, Feb. 6, 2002.

OMIM Database No. 604148, "Sodium-Dependent Dicarboxylate Transporter 1; NADC1", Jun. 11, 2002.

Rogina et al., "Cu, Zn superoxide dismutase deficiency accelerates the time course of an age-related marker in *Drosophila melanogaster*", *Biogerontology* 1:163-169 (2000).

Rogina et al., "Regulation of Gene Expression Is Linked to Life Span in Adult Drosophila", *Genetics* 141(3):1043-1048 (1995).

Rogina et al., "Spatial and temporal pattern of expression of the *wingless* and *engrailed* genes in the adult antenna is regulated by age-dependent mechanisms", *Mech. Dev.* 63:89-97 (1997).

Rogina et al., "Timing of Expression of a Gene in the Adult Drosophila Is Regulated by Mechanisms Independent of Temperature and Metabolic Rate", *Genetics* 143:1643-1651 (1996).

Rogina et al., "*Drosophila drop-dead* mutations accelerate the time course of age-related markers", *Proc. Natl. Acad. Sci. USA* 94:6303-6306 (1997).

Rogina et al., "Extended Life-Span Conferred by Cotransporter Gene Mutations in *Drosophila*", *Science* 290:2137-2140 (2000).

Rogina et al., "Regulation of gene expression is preserved in agin *Drosophila melanogaster*", *Current Biology* 8:475-478 (1998).

Sgró et al., "A Delayed Wave of Death from Reproduction in *Drosophila*", *Science* 286:2521-2523 (1999).

Adams et al., "The Genome Sequence of *Drosophila melanogaster*", *Science* 287:2185-2195 (2000).

Fleming et al., "Role of oxidative stress in Drosophila aging", *Mutation Research* 275:267-279 (1992).

Inoue et al., "Functional identity of *Drosophila melanogaster* Indy as a cation-independent, electroneutral transporter for tricarboxylic acid-cycle intermediates", *Biochem. J.* 367:313-319 (2002).

Khatri et al., "Cloning of the cDNA for a rat intestinal $Na^+$/dicarboxylate cotransporter reveals partial sequence homology with a rat intestinal mucin", *Biochimica et Biophysica Acta* 1309:58-62 (1996).

King et al., "Aging-Specific Expression of *Drosophila hsp22*", *Dev. Biol.* 207:107-118 (1999).

Kurapati et al., "Increased *hsp22* RNA Levels in *Drosophila* Lines Genetically Selected for Increased Longevity", *J. Gerontol Biol Sci.* 55A(11):B552-B559 (2000).

Roth et al., "Biomarkers of Caloric Restriction May Predict Longevity in Humans", *Science* 297:811 (2002).

Sun et al., "FLP Recombinase-Mediated Induction of Cu/Zn-Superoxide Dismutase Transgene Expression Can Extend the Life Span of Adult *Drosophila melanogaster* Flies", *Mol. Cell. Biol.* 19:216-228 (1999).

Tower, "Aging mechanisms in fruit flies", *BioEssays* 18(10):799-807 (1996).

Tower, "Transgenic methods for increasing *Drosophila* life span", *Mech Ageing Dev.* 118:1-14 (2000).

Lowman et al. "Selected high-affinity binding proteins by monovalent phage display." Biochemistry vol. 30, p. 10832-10838 (1991).

* cited by examiner

FIG. 1

Indy ORF atggaaattgaaattggcgaacaaccccagcctccggtgaagtgctccaacttcttcgctaaccactggaagggattggt
tgtgttcctggtgccgctgctatgtctgcctgttatgctgctaaacgaaggcgccgaatttcggtgcatgtacctccttt
tggtaatggccatattttgggttacggaagccttgcctctctatgtgacgtccatgataccgattgtggccttcccaata
atgggtataatgagctcggatcagacttgccgcttgtacttcaaggatacgctggtgatgttcatgggcggcattatggt
cgccctggctgtggagtactgtaatctacacaaacgtcttgccttgagggtaatccagatcgtgggctgcagtccccgca
gattacactttggcctcatcatggttacaatgttttgagcatgtggatttcgaacgccgcctgtactgccatgatgtgt
ccgattatccaagccgtgctggaggagctgcaggctcagggtgtctgcaaaatcaaccatgagcctcaataccaaatcgt
tggaggcaacaagaaaaacaacgaggatgagccaccatacccaccaagatcactctgtgctactatctgggcattgcct
acgcctcctcgctgggtggctgtggaaccatcatcggaactgccaccaatcttaccttcaagggcatctacgaggctcgt
ttcaagaactccaccgaacagatggacttccccaccttcatgttctactcggtgccatccatgttggtctacaccttgct
gacattcgtgttcctgcaatggcacttcatgggtctgtggcgtcccaagagcaaggaggcacaggaagtccagaggggac
gagagggcgccgatgtcgccaaaaaaggttatcgatcagcgctacaaggatctgggtcccatgtccattcacgagatccaa
gtgatgattctgttcattttatggttgtgatgtacttcacccgcaagcccggcatcttttgggatgggccgatttgct
gaattccaaggacattcgtaactctatgcccactattttgtcgtcgtcatgtgcttcatgctgcccgccaattatgctt
tcctacgctactgcaccagacgcggtggtccagtgcccacgggtcccactccatcgctgatcacctggaagttcatccag
accaaggtgccatggggtctggtgttcctgcttggcggtggcttcgcttttggccgaaggcagcaagcagagcggcatggc
caagctgattggcaatgctctgattggattgaaggttctgcccaactctgtcctcttactggtggtcatcctggtggctg
tgttcctgaccgccttcagctccaatgtggcgattgccaacattattattcccgttctggccgagatgtccctggccatt
gagatccatcctctgtacctgatcctgccgctggcttggcctgcagtatggccttccacctgccggttagtactccgcc
caacgctttggttgctggctatgccaacattaggacgaaggacatggccattgctggaatcggtccgaccatcattacca
tcatcaccctgtttgttttctgccaaacctggggcctggttgtctatccgaaccttaactcgttccccgaatgggctcag
atttatgccgcggcagcactgggaaacaagacgcactag

FIG. 2

MEIEIGEQPQPPVKCSNFFANHWKGLVVFLVPLLCLPVMLLNEGAEFRCM
YLLLVMAIFWVTEALPLYVTSMIPIVAFPIMGIMSSDQTCRLYFKDTLVM
FMGGIMVALAVEYCNLHKRLALRVIQIVGCSPRRLHFGLIMVTMFLSMWI
SNAACTAMMCPIIQAVLEELQAQGVCKINHEPQYQIVGGNKKNNEDEPPY
PTKITLCYYLGIAYASSLGGCGTIIGTATNLTFKGIYEARFKNSTEQMDF
PTFMFYSVPSMLVYTLLTFVFLQWHFMGLWRPKSKEAQEVQRGREGADVA
KKVIDQRYKDLGPMSIHEIQVMILFIFMVVMYFTRKPGIFLGWADLLNSK
DIRNSMPTIFVVVMCFMLPANYAFLRYCTRRGGPVPTGPTPSLITWKFIQ
TKVPWGLVFLLGGGFALAEGSKQSGMAKLIGNALIGLKVLPNSVLLLVVI
LVAVFLTAFSSNVAIANIIIPVLAEMSLAIEIHPLYLILPAGLACSMAFH
LPVSTPPNALVAGYANIRTKDMAIAGIGPTIITIITLFVFCQTWGLVVYP
NLNSFPEWAQIYAAAALGNKTH

POLYNUCLEOTIDES ENCODING CELLULAR TRANSPORTERS AND METHODS OF USE THEREOF

CROSS REFERENCE TO RELATED APPLICATIONS

This application claims priority from Provisional Application Ser. No. 60/255,013, filed Dec. 12, 2000, which is incorporated herein by reference in its entirety.

STATEMENT REGARDING FEDERALLY SPONSORED RESEARCH

The U.S. Government has certain rights in this invention pursuant to Grant Nos. AG14532, AG16667 awarded by the National Institute of Health, and 9728737 awarded by the National Science Foundation.

TECHNICAL FIELD

This disclosure relates generally to polynucleotides, the polypeptides, and proteins encoded by such polynucleotides, and methods of use of the polynucleotides, polypeptides, and proteins, particularly cellular transporters of carboxylates. This disclosure further relates to methods for screening candidate drug compounds for affecting cellular transporters of carboxylates, and to methods and compositions for the treatment and diagnosis of obesity, metabolic maintenance disorders, and the symptoms of aging. Specifically, this disclosure relates to methods of affecting the absorption, utilization, and/or storage of metabolites in a human or animal.

BRIEF DESCRIPTION OF THE RELATED ART

Obesity is a chronic disease highly prevalent in modern society, and is associated with decreased life span and numerous medical problems, including adverse psychological development, reproductive disorders such as polycystic ovarian disease, dermatological disorders such as infections, varicose veins, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease. Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. Considering the high prevalence and the serious consequences of obesity, any therapeutic method or drug potentially useful in reducing weight of obese persons could have a profound beneficial effect on their health. There accordingly remains a need for therapies that will reduce total body weight of obese subjects toward their ideal body weight without significant adverse side effects; that will help obese subjects maintain a reduced weight level; and, once treatment has begun, that will arrest the progression or prevent the onset of diseases that are the consequence of, or secondary to, the obesity, such as arteriosclerosis and polycystic ovarian disease.

One of the most important of these consequences is decreased life span. Caloric restriction (CR) is the only intervention known to dramatically extend life span in mammals. However, the likelihood that CR will be accepted as a general treatment to increase life span is vanishingly low. There accordingly further remains a need for acceptable therapies that will result life-span extension, again without significant adverse side effects.

SUMMARY OF THE INVENTION

Disclosed herein is an isolated polynucleotide selected from the group consisting of SEQ ID NO:1, SEQ ID NO:1 wherein T can also be U, and nucleic acid sequences substantially complementary to SEQ ID NO:1.

Also disclosed herein is an isolated polynucleotide encoding an amino acid sequence as set forth in SEQ ID NO:2, or variants of SEQ ID NO:2 comprising conservative amino acid substitutions of SEQ ID NO:2, wherein the variants retain the ability to function as cellular transporters of carboxylates. This disclosure further encompasses an isolated polynucleotide encoding a polypeptide having greater than or equal to 25% overall identity or greater than or equal to 30% overall similarity to SEQ ID NO:2, wherein the polypeptide is a cellular transporter of carboxylates.

Still further disclosed is a polypeptide having the sequence set forth in SEQ ID NO:2, as well as variants of SEQ ID NO:2 comprising conservative amino acid substitutions of SEQ ID NO:2, and polypeptide having greater than or equal to 25% overall identity or greater than or equal to 30% overall similarity to SEQ ID NO:2.

Further disclosed herein are methods for isolating an Indy gene comprising contacting a genomic library with one or more DNA probes under conditions effective to produce DNA or RNA copies of the Indy gene; producing copies of the Indy gene; identifying the copies; and isolating the copies; wherein the DNA probe comprises at least 14 contiguous nucleotides of SEQ ID NO:1.

Also disclosed is an expression vector comprising a polynucleotide selected from the group consisting of SEQ ID NO:1, SEQ ID NO:1 wherein T can also be U, and nucleic acid sequences fully complementary to SEQ ID NO:1, wherein the polynucleotide is operably linked to control sequences that direct transcription of the polynucleotide.

Also disclosed are methods of producing an INDY polypeptide comprising transforming a host cell with an expression vector comprising control sequences that direct transcription of the Indy polynucleotide; expressing the polynucleotide in a host cell; and recovering the INDY polypeptide.

Further disclosed herein is a method to assess the inhibitory activity of a test substance on a polypeptide having greater than or equal to 25% overall identity or greater than or equal to 30% overall similarity to SEQ ID NO:2, comprising contacting the cell with the test substance; and detecting the amount of carboxylate transported by the polypeptide in the presence and absence of the test substance; wherein inhibition of transport in the presence as compared to the absence of the test substance indicates that the test substance is a cellular transporter inhibitor.

Also disclosed are methods for decreasing the concentration of a polypeptide having greater than or equal to 25% overall identity or greater than or equal to 30% overall similarity to SEQ ID NO:2 in a cell or extract, comprising contacting the cell or extract with a first nucleic acid molecule in an amount effective to inhibit the expression of a second nucleic acid molecule expressing a cellular transporter of carboxylates, wherein the first nucleic acid molecule is substantially complementary to at least a portion of the Indy gene, and may be an antisense oligonucleotide, a ribozyme, a triple helix-forming molecule, a double stranded interfering RNA, or a mixture comprising at least one of the foregoing.

Further disclosed herein are methods of calorically restricting an organism, comprising administering to an organism an antagonist of the activity of a cellular transporter of carboxylates in an amount effective to inhibit the activity of the cellular transporter. Also disclosed are methods of extending life-span in an organism, comprising administering to an organism an antagonist of the activity of a cellular transporter of carboxylates in an amount effective to inhibit the activity of the cellular transporter.

Further disclosed are methods of treating an organism, comprising administering to an organism a vector encoding SEQ ID NO:1 or an active fragment thereof in an amount effective to increase the body weight of an organism.

BRIEF DESCRIPTION OF THE FIGURES

FIG. 1 shows the nucleotide sequence (SEQ ID NO:1) of Drosophila Indy. The full-length cDNA from the 'atg' initiation codon to the 'tag' stop codon is shown.

FIG. 2 shows the deduced amino acid sequence (SEQ ID NO:2) of the INDY polypeptide.

FIG. 9 shows the alignment of INDY with homologous proteins. The most homologous proteins to the INDY protein (Genbank accession AF217399; SEQ ID NO:2) were identified by Blast. Indy-2 is a highly homologous Drosophila gene (AE003728; SEQ ID NO:3). SDCT1 (AF058714; SEQ ID NO:4) and SDCT2 (AF081825; SEQ ID NO:5) are rat sodium dicarboxylate cotransporters, and hNaDC-1 (U26209; SEQ ID NO:6) is a human dicarboxylate cotransporter. The boxes indicate either identity or similarity to INDY.

DETAILED DESCRIPTION

The present disclosure originates from the discovery and cloning of a gene, the Indy gene, which is involved in increased life span in *Drosophila melanogaster*. As used herein the term "gene" means the segment of DNA involved in producing a polypeptide chain; it includes regions preceding and following the coding region (leader and trailer) as well as intervening sequences (introns) between individual coding segments (exons). The Indy gene encodes a polypeptide that has similarity to dicarboxylate transporters such as those from human and rat. Specifically, identification of Indy resulted from the observation that particular mutations in the gene cause an increase in the life span of the fly carrying the mutation. As a result of this finding, it is now possible to identify and/or isolate *Drosophila* lines with longer life spans, as well as to identify agents that contribute to longer life span. It is further possible to isolate the genes involved in and which have an effect on longevity, as well as the proteins encoded by these genes.

The Indy gene was identified from studies of *Drosophila* enhancer-trap lines, when it was observed that certain fly lines (namely lines 206 and 302) had extended life spans. The genomic DNA flanking the site of insertion in the enhancer-trap lines was sequenced. Both insertion sites were in the same gene that was named Indy.

Figure 3:
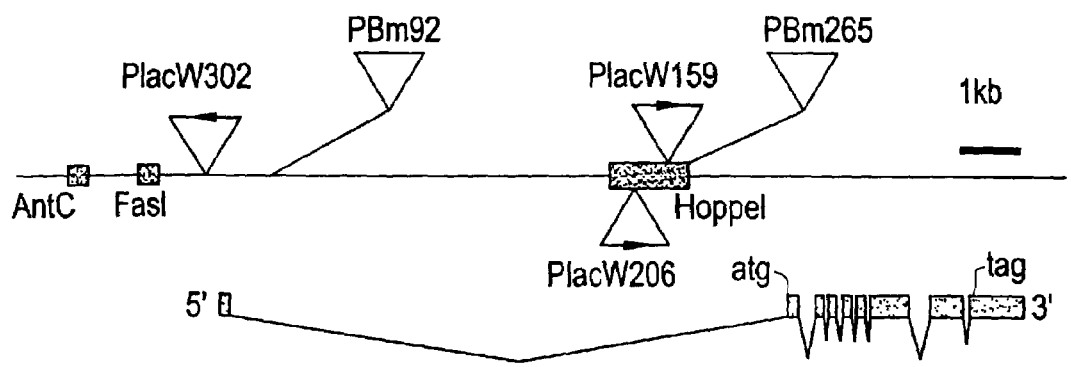
FIG. 3 shows the genomic organization of the Indy locus with the insertion sites of all five P-element alleles, wherein the black boxes represent conserved regulatory sequences; the gray box represents the conserved Hoppel transposable element; PlacW insertions sites in the 206, 302, and 159 insertion lines are shown, as well as orientation of the insertions; and positions of Birmingham-2 P-element insertions (PBm) in the 92 and 265 insertions lines are also shown.

The cDNA sequence and deduced amino acid sequence of Indy are shown in FIGS. 1 and 2, respectively. The genomic organization of the Indy gene is shown in FIG. 3. A cDNA encoding the open reading frame of Indy or portions thereof can be incorporated into commercially available bacterial expression plasmids such as the pGEM™ (Promega) or PBLUESCRIPT™ (Stratagene) vectors or one of their derivatives. When the Indy cDNA incorporated into a plasmid is transcribed by an appropriate RNA polymerase, the Indy mRNA is produced. The Indy mRNA is useful for in vivo and in vitro production of the INDY polypeptide.

Accordingly, in one embodiment, this disclosure provides an isolated polynucleotide sequence encoding the INDY polypeptide. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an automatically replicating plasmid or virus; or into the genomic DNA of a prokaryote or eukaryote, or which exists as a separate molecule (e.g., a cDNA) independent of other sequences. "Polynucleotide" or "nucleic acid sequence" refers to a polymeric form of nucleotides at least 5 bases in length. The nucleotides can be ribonucleotides, deoxyribonucleotides, or modified forms of either nucleotide. Modifications include but are not limited to known substitutions of a naturally-occurring base, sugar or internucleoside (backbone) linkage with a modified base such as 5-methylcytosine, a modified sugar such as 2'-methoxy and 2'-fluoro sugars, and modified backbones such as phosphorothioate and methyl phosphonate.

The polynucleotide can be a DNA molecule, a cDNA molecule, genomic DNA molecule, or an RNA molecule. The polynucleotide as DNA or RNA comprises a sequence wherein T can also be U. The polynucleotide can be complementary to SEQ ID NO:1, wherein complementary refers to the capacity for precise pairing between two nucleotides. For example, if a nucleotide at a certain position of a polynucleotide is capable of hydrogen bonding with a nucleotide at the same position in a DNA or RNA molecule, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process. As used herein, hybridization means hydrogen bonding, which may be Watson-Crick, Hoogsteen or reversed Hoogsteen hydrogen bonding, between complementary nucleoside or nucleotide bases.

In addition, polynucleotides encoding all or a portion of Indy are included, so long as they encode a polypeptide with INDY activity, such as increased lifespan. Such polynucleotides include naturally occurring, synthetic and intentionally manipulated DNA molecules. For example, the Indy polynucleotide may be subjected to site-directed mutagenesis by techniques known in the molecular biology art. There are 20 naturally occurring amino acids, most of which are specified by more than one codon. Therefore, degenerate nucleotide sequences are included as long as the INDY polypeptide encoded by the nucleotide sequence is functionally unchanged. Also included are polynucleotide sequences that encode amino acid sequences which differ from those of the Indy gene, but which should not produce phenotypic changes.

The Indy polynucleotides also include polynucleotides coding for polypeptide analogs, fragments or derivatives of antigenic polypeptides which differ from naturally-occurring Indy forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptide) and which share some or all properties of naturally-occurring forms. These molecules include the incorporation of codons suitable for expression by selected non-mammalian hosts; the provision of sites for cleavage by restriction endonuclease enzymes; and the provision of additional initial, terminal or intermediate DNA sequences that facilitate construction of readily expressed vectors.

The Indy polynucleotides include polynucleotides that encode INDY polypeptides or full-length protein that contain substitutions, insertions, or deletions into the protein backbone. Related polypeptides are aligned with INDY by assigning degrees of homology to various deletions, substitutions and other modifications. Homology can be determined along the entire polypeptide or polynucleotide or along subsets of contiguous residues. The percent identity is the percentage of amino acids or nucleotides that are identical when the two sequences are compared. The percent similarity is the percentage of amino acids or nucleotides that are chemically similar when the two sequences are compared. INDY and a homologous polypeptide are preferably greater than or equal to 25%, preferably greater than or equal to 30%, more preferably greater than or equal to 35% or most preferably greater than or equal to 40% identical. INDY and a homologous polypeptide are preferably greater than or equal to 30%, preferably greater than or equal to 35%, more preferably greater than or equal to 45% similar.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

The polynucleotide includes SEQ ID NO:1 as well as complementary sequences to that sequence. When the sequence is RNA, the nucleotide T in SEQ ID NO:1 is U. In addition, polynucleotides that are substantially identical to SEQ ID NO:1 or which encode proteins substantially identical to SEQ ID NO:2 are included. By "substantially identical" is meant a polypeptide or polynucleotide having a sequence that is at least 85%, preferably 90%, and more preferably 95% or more identical to the sequence of the reference amino acid or nucleic acid sequence. For polypeptides, the length of the reference polypeptide sequence will generally be at least 16 amino acids, preferably at least 20 amino acids, more preferably at least 25 amino acids, and most preferably at least 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

Sequence identity and similarity can be measured using sequence analysis software (e.g., Sequence Analysis Software Package of the Genetics Computer Group, University of Wisconsin Biotechnology Center, 1710 University Avenue, Madison, Wis. 53705) with the default parameters specified therein.

This disclosure also encompasses DNAs and cDNAs that hybridize to the Indy polynucleotide. Hybridization methods are well known to those of ordinary skill in the art. The hybridizing sequences can be nucleic acid sequences of greater than about 14 nucleotides in length that selectively hybridize to an Indy polynucleotide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

The Indy polynucleotide can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on Nickel columns. Such gene modification techniques and suitable additional sequences are well known in the molecular biology arts.

The Indy polynucleotide can be inserted into a recombinant DNA vector for production of Indy mRNA. Such vectors may be used for the in vitro or in vivo production of Indy mRNA. For in vitro production of Indy mRNA, the cDNA comprising SEQ ID NO:1, for example, is inserted into a plasmid containing a promoter for either SP6 or T7 RNA polymerase. The plasmid is cut with a restriction endonuclease to allow run-off transcription of the mRNA, and the RNA is produced by addition of the appropriate buffer, ribonucleotides, and polymerase. The RNA is isolated by conventional means such as ethanol precipitation. The mRNA can be capped or polyadenylated, for example, prior to injection into a cell such as a *Xenopus* oocyte.

The Indy polynucleotide can be inserted into a recombinant expression vector. The term "recombinant expression vector" refers to a plasmid, virus, or other means known in the art that has been manipulated by insertion or incorporation of the Indy genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide having the biological activity of a cellular transporter. Suitable hosts include microbes such as bacteria, yeast, insect or mammalian organisms or cell lines.

The Indy genetic sequence can be inserted into a vector adapted for expression in a bacterial, yeast, insect, amphibian, or mammalian cell that further comprises the regulatory elements necessary for expression of the nucleic acid molecule in the bacterial, yeast, insect, amphibian, or mammalian cell operatively linked to the nucleic acid molecule encoding a cellular transporter of carboxylates as to permit expression thereof. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., atg) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153: 516–544, 1987).

Examples of suitable bacteria are *E. coli* and *B.subtilis*. A preferred yeast vector is pRS426-Gal. Examples of suitable yeast are *Saccaromyces* and *Pichia*. Suitable amphibian cells are *Xenopus* cells. Suitable vectors for insect cell lines include baculovirus vectors. Rat or human cells are preferred mammalian cells.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., an INDY polypeptide), or fragment thereof.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of this disclosure, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*) or may be a mammalian cell, including a human cell.

Mammalian cell systems that utilize recombinant viruses or viral elements to direct expression may be engineered. For example, when using adenovirus expression vectors, the nucleic acid sequences encoding a foreign protein may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the INDY polypeptide in infected hosts (e.g., Logan & Shenk, *Proc. Natl. Acad. Sci. U.S.A.* 81:3655–3659, 1984).

For long-term, high-yield production of recombinant proteins, stable expression is preferred. Rather than using expression vectors that contain viral origins of replication, host cells can be transformed with the cDNA encoding an INDY fusion protein controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1 to 2 days in an enriched media, and then are switched to a selective media. A number of selection systems may be used, including but not limited to the herpes simplex virus thymidine kinase (Wigler et al., *Cell* 11: 233, 1977), hypoxanthine-guanine phosphoribosyltransferase (Szybalska & Szybalski, *Proc. Natl. Sci. U.S.A.* 48: 2026, 1962), and adenine phosphoribosyltransferase (Lowy et al., *Cell* 22: 817, 1980) genes can be employed in $t^k$, $hg^{prt}$ or $a^{prt}$ cells respectively.

Among the known methods for expressing transporter genes is expression in a *Xenopus* oocyte system. A cDNA encoding the open reading frame of Indy or portions thereof can be incorporated into commercially available bacterial expression plasmids such as the pGEM (Promega) or pBluescript (Stratagene) vectors or one of their derivatives. After amplifying the expression plasmid in bacterial (*E. coli*) cells the DNA is purified by standard methods. The incorporated transporter sequences in the plasmid DNA are then transcribed in vitro according to standard protocols, such as transcription with SP6 or T7 RNA polymerase. The RNA thus prepared is injected into *Xenopus* oocytes where it is translated and the resulting transporter polypeptides are incorporated into the plasma membrane. The functional properties of these transporters can then be investigated by electrophysiological, biochemical, pharmacological, and related methods.

In addition to the Indy sequences described above, full-length Indy cDNA, gene sequences or paralogs present in the same species or orthologs of the Indy gene in other species can readily be identified without undue experimentation, by molecular biological techniques well known in the art. The identification of orthologs of Indy can be useful for developing model animal systems more closely related to humans for use in drug design. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species, and "paralog" meaning a functionally similar sequence when considered within the same species.

Genes that contribute to increased life span or senescence can be isolated by isolation of DNA homologous to other genes known to contribute to increased life span, for example the Indy gene. A gene library from an organism of interest can be probed using protocols well known in the art. The gene library is preferably a mammalian gene library and more preferably a human gene library. Homologous genes can be isolated by hybridization. For example, a labeled DNA fragment comprising the Indy gene is used to probe cellular DNA from an organism of interest under high, medium or low hybridization stringency conditions, depending on the degree of homology sought, for example as taught in Sambrook et al., Eds., *Molecular Cloning: A Laboratory Manual,* 2nd ed., Cold Spring Harbor Laboratory Press, 1989, or Ausubel, F. M. et al., eds. *Current Protocols in Molecular Biology,* 1994. DNA hybridizing to the probe is isolated, and complementation analysis is performed to verify that the DNA comprises a gene that contributes to longevity. DNA from an organism of interest can be hybridized under high stringency conditions to DNA comprising a mutated Indy gene. A preferred Indy DNA probe is greater than or equal to 14 contiguous nucleotides of SEQ ID NO:1.

Homologous genes can also be found by the polymerase chain reaction (PCR) (see Sakai et al., *Science* 230: 1350–4, 1985; and Sakai et al., *Science* 239: 487–91, 1988). Synthetic oligonucleotide primers that comprise regions of the Indy gene can be used. The term "oligonucleotide" as used herein is defined as a molecule comprising 2 or more deoxyribonucleotides or ribonucleotides, preferably more than 3, and most preferably more than about 10. Further as used herein the term "oligonucleotide" comprises less than about 100, more preferably less than about 80, most preferably less than about 50 deoxyribonucleotides or ribonucleotides. The exact size of an oligonucleotide will depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., *Meth. Enzymol.* 68: 90–99, 1979; the phosphodiester method of Brown et al., *Method Enzymol.* 68: 109–151, 1979, the diethylphosphoramidite method of Beaucage et al, *Tetrahedron Lett.* 22: 1859–1862, 1981; the triester method of Matteucci et al., *J. Am. Chem. Soc.* 103: 3185–3191, 1981, or automated synthesis methods; and the solid support method of U.S. Pat. No. 4,458,066.

The term "primer" as used herein refers to an oligonucleotide that is capable of acting as a point of initiation of synthesis when placed under conditions in which primer extension is initiated or possible. Synthesis of a primer extension product that is complementary to a nucleic acid strand is initiated in the presence of nucleoside triphosphates and a polymerase in an appropriate buffer at a suitable temperature. The term primer may refer to more than one primer, particularly in the case where there is some ambiguity in the information regarding one or both ends of the target region to be synthesized. For instance, if a nucleic acid sequence is inferred from a protein sequence, a primer generated to synthesize nucleic acid encoding said protein sequence is actually a collection of primer oligonucleotides containing sequences representing all possible codon variations based on the degeneracy of the genetic code. One or more of the primers in this collection will be homologous with the end of the target sequence. Likewise, if a "conversed" region shows significant levels of polymorphism in a population, mixtures of primers can be prepared that will amplify adjacent sequences. For example, primers can be synthesized based upon the amino acid sequence as set forth in SEQ ID NO:2 and can be designed based upon the degeneracy of the genetic code.

In one embodiment, synthetic oligonucleotide primers that comprise the region of the Indy gene that contains a mutation are used. Alternatively, oligonucleotides can be patterned after any gene, such as those isolated by this method or any of the above methods, which contributes to senescence or to longer life span. The oligonucleotides are utilized in PCR to generate multiple copies of DNA of interest from a sample of genomic DNA from the organism of interest. The DNA multiplied in PCR is then isolated, and complementation analysis is performed to verify that the DNA comprises a functional gene that contributes to senescence or to longer life span. Once genes have been isolated using these methods, standard procedures can then be used to isolate the proteins encoded by the genes.

Homologous genes can also be found by computerized database searches to identify genes that include regions of homology to the Indy or other homologous genes. Sequence analysis software matches the similar sequences by assigning degrees of homology to various deletions, substitutions and other modifications. Homologous or identical sequences have a specified percentage of amino acid residues or nucleotides the same when aligned for maximal correspondence over a specified comparison window. The comparison window can be 20 to 600 nucleotides or amino acids. A useful program is BLAST, which is described in Atschul et al., *Nucl. Acids Res.* 25: 3389–3402, 1977; and Atschul et al., *J Mol. Biol.* 215: 403–410, 1990.

In a separate embodiment, the polynucleotide encodes a sequence having substantial homology with human sodium dicarboxylate cotransporters (hNaDC-1, accession No. U26209), rat sodium dicarboxylate cotransporters (SDCT2, accession no. AF081825), rabbit sodium dicarboxylate cotransporters (NaDC-1, accession no. U12186) and mouse sodium dicarboxylate cotransporters (mNaDC-1, accession no. AF 201903).

The polynucleotides described and claimed herein are useful for the information that they provide concerning the amino acid sequence of the polypeptide and as products for the large scale synthesis of the polypeptide by a variety of recombinant techniques. The polynucleotides are useful for generating new cloning and expression vectors, transformed and transfected prokaryotic and eukaryotic host cells, and new and useful methods for cultured growth of such host cells capable of expression of the polypeptide and related products.

The Indy gene codes for a polypeptide or protein having the sequence shown in FIG. 2 (SEQ ID NO:2, genBank accession no. AE003519), such sequence having substantial homology with a *Drosophila* gene (accession no. AF217399), human sodium dicarboxylate cotransporters (hNaDC-1, accession No. U26209) and rat sodium dicarboxylate cotransporters (SDCT2, accession no. AF081825, and SDCT1, accession no. AF058714). The Indy gene product and the family of cellular transporters in mammals appears to define a new class of gene products involved in determining life span and metabolic control.

Accordingly in another embodiment, there is provided a substantially pure polypeptide homologous to SEQ ID NO:2. A "substantially pure polypeptide" is an INDY polypeptide that has been separated from components that naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, INDY polypeptide. A substantially pure INDY polypeptide may be obtained, for example, by extraction from a natural source (e.g., an insect cell); by expression of a recombinant nucleic acid encoding an INDY polypeptide; or by chemically synthesizing the protein. Purity can be measured by any appropriate method, e.g., by column chromatography, polyacrylamide gel electrophoresis, or by HPLC analysis.

Amino acids essential for the function of INDY polypeptides can be identified according to procedures known in the art, such as site-directed mutagenesis or alanine-scanning mutagenesis (Cunningham and Wells, *Science* 244: 1081–1085, 1989; Bass et al., *Proc. Natl. Acad. Sci. USA* 88: 4498–4502, 1991). In the latter technique, single alanine mutations are introduced at different residues in the molecule, and the resultant mutant molecules are tested for biological activity (e.g., ligand binding and signal transduction) to identify amino acid residues that are critical to the activity of the molecule. Sites of ligand-protein interaction can also be determined by analysis of crystal structure as determined by such techniques as nuclear magnetic resonance, crystallography or photoaffinity labeling. (See, for example, de Vos et al., *Science* 255: 306–312, 1992; Smith et al., *J. Mol. Biol.* 224: 899–904, 1992; Wlodaver et al., *FEBS Lett.* 309: 59–64, 1992). The identities of essential amino acids can also be inferred from analysis of homologies with related proteins.

Multiple amino acid substitutions can be made and tested using known methods of mutagenesis and screening, such as those disclosed by Reidhaar-Olson and Sauer, *Science* 241: 53–57, 1988; or Bowie and Sauer, *Proc. Natl. Acad. Sci. USA* 86: 2152–2156, 1989. Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30: 10832–10837, 1991; Ladner et al., U.S. Pat. No. 5,223,409; Huse, WIPO Publication WO 92/06204) and region-directed mutagenesis (Derbyshire et al., *Gene* 46: 145, 1986; Ner et al., *DNA* 7: 127, 1988).

Mutagenesis methods as disclosed above can be combined with high-throughput screening methods to detect the activity of cloned, mutagenized proteins in host cells. Mutagenized DNA molecules that encode active proteins or portions thereof (e.g., ligand-binding fragments) can be recovered from the host cells and rapidly sequenced using modem equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to SEQ ID NO:2 or allelic variants thereof and retain the properties of the wild-type polypeptide. As expressed and claimed herein the language, "a polypeptide as defined by SEQ ID NO: 2" includes all allelic variants and species orthologs of the polypeptide. When the amino acids forming the sequence are alpha-amino acids, either the L-optical isomer or the D-optical isomer can be used, the L-isomers being preferred. The term "polypeptide" as used herein includes modified sequences such as glycoproteins, and is specifically intended to cover naturally occurring polypeptides or proteins, as well as those that are recombinantly or synthetically synthesized, which occur in at least two different conformations wherein both conformations have the same or substantially the same amino acid sequence but have different three dimensional structures. "Fragments" are a portion of a naturally occurring protein. Fragments can have the same or substantially the same amino acid sequence as the naturally occurring protein.

INDY polypeptides and peptide fragments including mutated, truncated or deleted forms can be prepared for a variety of uses including generation of antibodies, as reagents in diagnostic assays, for the identification of other gene products involved in the regulation of life span and body weight, as reagents for screening for compounds that can be used in the extension of life span or body weight control and as pharmaceutical treatments useful for extension of lifespan or for treatment of body weight disorders.

The disclosure also encompasses proteins that are functionally equivalent to the Indy gene product, as judged by any of a number of criteria, including but not limited to the resulting biological effect of Indy, for example, life-span extension and caloric restriction or change in phenotype when the Indy equivalent is present in an appropriate cell type. Such functionally equivalent INDY proteins include additions or substitutions of amino acid residues within the amino acid sequence encoded by the Indy nucleotide sequences described, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Another embodiment comprises antibodies that specifically recognize one or more epitopes of INDY or conserved variants of INDY or fragments of INDY. Such antibodies may be polyclonal antibodies, monoclonal antibodies, humanized or chimeric antibodies, anti-idiotypic antibodies, single chain antibodies, Fab fragments, fragments produced from an Fab expression library, and epitope-binding fragments of the above.

Antibodies that bind to the INDY polypeptide can be prepared from the intact polypeptide or fragments containing peptides of interest as the immunizing agent. A preferred INDY polypeptide fragment is 15–30 contiguous amino acids of SEQ ID NO:2. The preparation of polyclonal antibodies is well known in the molecular biology art; see for example, *Production of Polyclonal Antisera in Immunochemical Processes* (Manson, ed.), pages 1–5 (Humana Press 1992) and Coligan et al., *Production of Polyclonal Antisera in Rabbits, Rats, Mice and Hamsters in Current Protocols in Immunology*, section 2.4.1 (1992). The preparation of monoclonal antibodies is also well known in the art; see for example, Harlow et al., *Antibodies: A Laboratory Manual*, page 726 (Cold Spring Harbor Pub. 1988). Briefly, monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridomal cultures by techniques well known in the art.

A therapeutically useful anti-INDY antibody may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., *Nature* 321: 522, 1986 and Singer et al., *J. Immunol.* 150: 2844, 1993. The antibodies can also be derived from human antibody fragments isolated from a combinatorial immunoglobulin library; see, for example, Barbas et al., *Methods: A Companion to Methods in Enzymology* 2, 119, 1991.

In addition, chimeric antibodies can be obtained by splicing the genes from a mouse antibody molecule with appropriate antigen specificity together with genes from a human antibody molecule of appropriate biological specificity; see, for example, Takeda et al., *Nature* 314: 544–546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies against Indy gene products, as described, for example, in U.S. Pat. No. 4,946,778. Single chain antibodies are formed by linking the heavy and light chain fragments of the Fv region via an amino acid bridge, resulting in a single chain polypeptide.

Antibody fragments that recognize specific epitopes can be generated by techniques well known in the art. Such fragments include Fab fragments produced by proteolytic digestion, and Fab fragments generated by reducing disulfide bridges.

When used for immunotherapy, the monoclonal antibodies, fragments thereof, or both, that bind to INDY may be unlabelled or labeled with a therapeutic agent. These agents can be coupled directly or indirectly to the monoclonal antibody by techniques well known in the art, and include such agents as drugs, radioisotopes, lectins and toxins.

The monoclonal antibodies can be used alone or in combination with therapeutic agents such as those described above. Preferred combinations include monoclonal antibodies that bind INDY and immunomodulators and other biological response modifiers. The dosage ranges for the administration of monoclonal antibodies are large enough to produce the desired effect, either a change in life span or change in body weight. The dosage will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, subcutaneously, intracavity, or transdermally, alone or with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The human homolog of Indy is normally expressed in the gut, kidney, liver, brain and other organs, and can be easily targeted pharmacologically. The novelty in the discovery of the Indy gene lies in the fact that Indy mutants may be genetically calorically restricted, allowing them to eat normally, maintain high levels of physical activity and reproductive status, while benefiting from increased life span. The discovery of Indy mutant animals has identified a target to which appropriate therapeutic agents could be designed to provide a chemical intervention. Such drugs could potentially block the uptake of key metabolites by INDY protein, and, at appropriate doses, provide the benefit of increased longevity through a form of caloric restriction. Such INDY-based agents would also have potential benefit in the control of ideal body weight. Because the INDY protein is an accessible target (for instance, it may have a primary role in absorbing, utilizing and/or storing metabolites), such INDY-drugs could be designed to have low absorption/toxicity affects and potentially exert their largest effects in a non-invasive, controlled ambush of a fraction of a person's intake of nutrients. There may also be undiscovered naturally occurring substances that block INDY function.

Without being bound by theory, it appears that the Indy gene encodes a cellular transporter that transports key intermediates of the Krebs or citric acid cycle. The transported intermediates include organic carboxylates, more particularly substituted and unsubstituted dicarboxylates having from two to about ten, preferably four to about six carbon atoms such as succinate, alpha-ketoglutarate and fumarate; and substituted and unsubstituted tricarboxylates having from three to about ten, preferably four to about carbon atoms, for example citrate. Suitable substitutions include but are not limited to hydroxyl groups, carbonyl groups, sulfhydryl groups, and the like. Unsaturation may also be present. A preferred substrate for INDY is succinate. It is to be understood that although reference is made to the ionized form of the acids, the protonated acid or another conjugated form may actually be transported. INDY is thus described as a cellular transporter of carboxylates, particularly di- and tricarboxylates.

Experimental evidence indicates that unlike other transporters of Krebs cycle intermediates (the sodium dicarboxylate cotransporters, for example), INDY does not appear to require monovalent cations to transport its substrates. INDY is thus referred to herein as a "transporter". However, this term does not exclude any form of the Indy gene product that in fact co-transports other moieties along with the carboxylates, for example divalent cations.

Described below are methods and compositions whereby metabolic disorders, obesity, or aging symptoms may be ameliorated. Certain of these states may be brought about, at least in part, by an excessive level of Indy gene product, or by the presence of a gene product exhibiting an abnormal or excessive activity. As such, the reduction in the level and/or activity of such gene products would bring about the amelioration of symptoms, for example, in hyperglycemic conditions, diabetes, and chronic obesity. A variety of techniques may be utilized to inhibit the expression, synthesis, or activity of such target genes and/or proteins. For example, compounds and large molecules that exhibit inhibitory activity may be used in accordance with this disclosure to ameliorate metabolic disorders, obesity, or aging symptoms. Such molecules may include, but are not limited to small organic molecules, peptides, antibodies, antisense, ribozyme molecules, triple helix molecules, and the like.

The following assays provide methods (also referred to herein as a "screening assay") for identifying modulators, i.e., candidate or test compounds or agents (e.g., peptides, peptidomimetics, small molecules or other drugs) which bind to the INDY polypeptide, have a stimulatory or inhibitory effect on, for example, Indy expression or INDY activity, or have a stimulatory or inhibitory effect on, for example, the expression or activity of an INDY substrate. Such compounds can be agonists or antagonists of INDY function.

One embodiment herein accordingly comprises methods for the identification of small molecule drug candidates from large libraries of compounds that appear to have therapeutic activity to affect metabolic maintenance and/or to reverse or prevent cell death and thus exhibits potential therapeutic utility enhancing longevity. Small organic molecules and peptides having effective inhibitory activity may be designed de novo, identified through assays or screens, or obtained by a combination of the two techniques. Non-protein drug design may be carried out using computer graphic modeling to design non-peptide, organic molecules able to bind to the cellular transporters. The use of nuclear magnetic resonance (NMR) data for modeling is also known in the art, as described by Lam et al., Science 263: 380, 1994, using information from x-ray crystal structure studies of the transporter.

Small molecules may also be developed by generating a library of molecules, selecting for those molecules which act as ligands for a specified target, (using protein functional assays, for example), and identifying the selected ligands. See, e.g., Kohl et al., Science 260: 1934, 1993. Techniques for constructing and screening combinatorial libraries of small molecules or oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, 7 Feb. 1994) and nonpeptide polymers (see, e.g., "peptoids" of Simon et al., *Proc. Natl. Acad. Sci. USA* 89 9367, 1992). See also U.S. Pat. No. 5,270,170 to Schatz; Scott and Smith, *Science* 249: 386–390, 1990; Devlin et al., *Science* 249: 404–406, 1990; Edgington, *BIO/Technology*, 11: 285, 1993. Libraries may be synthesized in solution on solid supports, or expressed on the surface of bacteriophage viruses (phage display libraries).

Known screening methods may be used by those skilled in the art to screen combinatorial libraries to identify active molecules. For example, an increase (or decrease) in active uptake of a nutrient due to contact with a transporter agonist or antagonist can be monitored.

In one embodiment, assays for screening candidate or test compounds that are substrates of an INDY protein or polypeptide or biologically active portion thereof are provided. In another embodiment, assays for screening candidate or test compounds which bind to or modulate the activity of an INDY protein or polypeptide or biologically active portion thereof; e.g., modulate the ability of INDY to interact with a ligand.

Examples of methods for the synthesis of molecular libraries can be found in the art, for example in: DeWitt et al., *Proc. Natl. Acad. Sci. U.S.A.* 90: 6909, 1993; Erb. et al., *Proc. Natl. Acad. Sci. USA* 91: 11422, 1994; Zuckermann et al., *J. Med. Chem.* 37: 2678, 1994; Cho et al., *Science* 261: 1303, 1993; Carrell et al., *Angew. Chem. Int. Ed. Engl.* 33: 2059, 1994; Carell et al., *Angew. Chem. Int. Ed. Engl.* 33: 2061, 1994; and in Gallop et al., *J. Med. Chem.* 37: 1233, 1994.

Libraries of compounds may be presented in solution (e.g., Houghten, *Biotechniques* 13: 412–421, 1992), or on beads (Lam, *Nature* 354: 82–84, 1991), chips (Fodor, *Nature* 364: 555–556, 1993), bacteria (Ladner U.S. Pat. No. 5,223,409), spores (Ladner U.S. Pat. No. '409), plasmids (Cull et al., *Proc Natl Acad Sci USA* 89: 1865–1869, 1992) or on phage (Scott and Smith, *Science* 249: 386–390, 1990); (Devlin, *Science* 249: 404–406, 1990); (Cwirla et al., *Proc. Natl. Acad. Sci U.S.A.* 87: 6378–6382, 1990); (Felici, *J. Mol. Biol.* 222: 301–310, 1991); (Ladner supra.).

Candidate INDY interacting molecules encompass many chemical classes. They can be organic molecules, preferably small organic compounds having molecular weights of 50 to 2,500 daltons. The candidate molecules comprise functional groups necessary for structural interaction with proteins, particularly hydrogen bonding, for example, carbonyl, hydroxyl, and carboxyl groups. The candidate molecules can comprise cyclic carbon or heterocyclic structures and aromatic or polyaromatic structures substituted with the above groups.

Other techniques are known in the art for screening synthesized molecules to select those with the desired activity, and for labeling the members of the library so that selected active molecules may be identified, as in U.S. Pat. No. 5,283,173 to Fields et al., (use of genetically altered *Saccharomyces* cerevisiae to screen peptides for interactions). As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized fragments that are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology* 11: 285, 1993. U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA* 89: 8864, 1992; and Tsai and Keene, *J. Immunology* 150: 1137, 1993. In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

Antibodies that are both specific for target gene protein and interfere with its activity may be used to inhibit target gene function. Such antibodies may be generated using standard techniques, against the proteins themselves or against peptides corresponding to portions of the proteins. Such antibodies include but are not limited to polyclonal, monoclonal, Fab fragments, single chain antibodies, chimeric antibodies, and the like. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (e.g., see Sambrook et al., Eds., *Molecular Cloning: A Laboratory Manual*, 2nd ed., Cold Spring Harbor Laboratory Press, 1989, or Ausubel, F. M. et al., eds. *Current Protocols in Molecular Biology*, 1994).

Alternatively, single chain neutralizing antibodies that bind to intracellular target gene epitopes may also be administered. Such single chain antibodies may be administered, for example, by expressing nucleotide sequences encoding single-chain antibodies within the target cell population by utilizing, for example, techniques such as those described in Marasco et al., *Proc. Natl. Acad. Sci. USA* 90: 7889–7893, 1993.

Also encompassed are assays for cellular proteins that interact with INDY. Any method suitable for detecting protein-protein interactions may be used. The traditional methods that may be used include, for example, co-immunoprecipitation, crosslinking, and co-purification through gradients or chromatographic columns. For these assays, Indy can be a full-length protein or an active fragment. Additional methods include those methods that allow for the simultaneous identification of genes that encode proteins that interact with INDY. These methods include, for example, probing expression libraries using a labeled INDY protein, INDY fragment, or INDY fusion protein.

One method to detect protein-protein interaction in vivo is the two-hybrid system, see, for example, Chien et al., *Proc. Natl. Acad. Sci, USA* 88: 9578–9582, 1991. In brief, the two-hybrid system utilizes plasmids constructed to encode two hybrid proteins: one plasmid comprises the nucleotides encoding the DNA binding domain of a transcriptional activator protein fused to the Indy nucleotide sequence encoding the INDY polypeptide, and the other plasmid comprises the nucleotides encoding the transcriptional activator protein's activation domain fused to a cDNA encoding an unknown protein that has been recombined into the plasmid from a cDNA library. The DNA binding domain fusion plasmid and the cDNA fusion protein library plasmids are transformed into a strain of yeast that contains a reporter gene, for example lacZ, whose regulatory region contains the activator's binding site. Either hybrid protein alone cannot activate translation of the reporter gene because it is lacking either the DNA binding domain or the activator domain. Interaction of the two hybrid proteins, however, reconstitutes a functional activator protein and results in activation of the reporter gene that is detected by an assay for the reporter gene product. The colonies that reconstitute activator activity are purified and the library plasmids responsible for reporter gene activity are isolated and sequenced. The DNA sequence is then used to identify the protein encoded by the library plasmid.

Macromolecules that interact with INDY are referred to as Indy binding partners. Indy binding partners are likely to be involved in the regulation of INDY function. Therefore, it is possible to identify compounds that interfere with the interaction between INDY and its binding partners. The basic principle of assay systems used to identify compounds that interfere with the interaction of Indy and a binding partner is to prepare a reaction mixture containing INDY or an INDY fragment and the binding partner under conditions that allow complex formation. The reaction mixture is prepared in the presence or absence of the test compound to test for inhibitory activity. The test compound may be added prior to or subsequent to INDY/binding partner complex formation. The formation of a complex in a control but not with the test compound confirms that the test compound interferes with complex formation. The assay can be conducted either in the solid phase or in the liquid phase.

In another embodiment, an assay is a cell-based assay comprising contacting a cell expressing INDY with a test compound and determining the ability of the test compound to modulate (e.g. stimulate or inhibit) the activity of INDY. A preferred activity is the transporter function of INDY. Determining the ability of the test compound to modulate the activity of INDY can be accomplished, for example, by determining the ability of INDY to bind to or interact with the test molecule, or by determining the ability of the test molecule to stimulate or inhibit the transporter function of INDY. Cell-based systems can be used to identify compounds that inhibit INDY. Such cells can be recombinant or non-recombinant, such as cell lines that express the Indy gene. Preferred systems are *Xenopus* oocytes containing the Indy mRNA and yeast cells that express Indy. In utilizing such systems, cells are exposed to compounds suspected of ameliorating body weight disorders or increasing lifespan. After exposure, the cells are assayed, for example, for expression of the Indy gene or the INDY protein. Alternatively, the cells are assayed for phenotypes such as those resembling body weight disorders or lifespan extension. The cells may also be assayed for the inhibition of the transporter function of INDY.

A preferred cell for use in a cell-free assay comprises a *Xenopus* oocyte containing the Indy mRNA. Such *Xenopus* oocytes will express the INDY polypeptide and can be used to study the transporter function of INDY. A *Xenopus* oocyte expressing the INDY polypeptide is useful for screening test compounds for alteration in INDY function. Compounds that either increase or decrease the transport of Krebs cycle intermediates by INDY can be identified in this system.

Another preferred cell for a cell-based assay comprises a yeast cell transformed with a vector comprising the Indy gene. One use for a yeast cell expressing Indy is to mutagenize the yeast and screen for yeast that will survive only when the INDY polypeptide is functioning normally. Synthetic lethal screens are described in Holtzman et al., *J. Cell Bio.* 122: 635–644, 1993. The yeast that require Indy function for survival can then be used to screen test compounds for those that inhibit Indy activity. Test compounds that results in a decrease in yeast survival are likely inhibitors of INDY in this system.

In yet another embodiment, an assay is a cell-free assay in which an INDY protein or biologically active portion thereof is contacted with a test compound and the ability of the test compound to bind to the INDY protein or biologically active portion thereof is determined. Binding of the test compound to the INDY protein can be determined either directly or indirectly as described above. In a preferred embodiment, the assay includes contacting the INDY protein or biologically active portion thereof with a known compound which binds INDY to form an assay mixture, contacting the assay mixture with a test compound, and determining the ability of the test compound to interact with an INDY protein, wherein determining the ability of the test compound to interact with an INDY protein comprises determining the ability of the test compound to preferentially bind to INDY or a biologically active portion thereof as compared to the known compound.

The cell-free assays are amenable to use of both soluble and/or membrane-bound forms of proteins. In the case of cell-free assays in which a membrane-bound form of the protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl,N,N-dimethyl-3-ammonio-1-propane sulfonate.

In more than one embodiment of the above assay methods, it may be desirable to immobilize either INDY or its target molecule to facilitate separation of complexed from uncomplexed forms of one or both of the proteins, as well as to accommodate automation of the assay. Binding of a test compound to an INDY protein, or interaction of an INDY protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/INDY fusion proteins or glutathione-S-transferase/target fusion proteins can be adsorbed onto glutathione SEPHAROSE® beads (Sigma Chemical, St. Louis, Mo.) or glutathione derivatized microtitre plates, which are then combined with the test compound or the test compound and either the non-adsorbed target protein or INDY protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of INDY binding or activity determined using standard techniques.

Other techniques for immobilizing proteins on matrices can also be used in the screening assays of the invention. For example, either an INDY protein or an INDY target molecule can be immobilized utilizing conjugation of biotin and streptavidin. Biotinylated INDY protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with INDY protein or target molecules but which do not interfere with binding of the INDY protein to its target molecule can be derivatized to the wells of the plate, and unbound target INDY protein trapped in the wells by antibody conjugation. Methods for detecting such complexes, in addition to those described above for the GST-immobilized complexes, include immunodetection of complexes using antibodies reactive with the INDY protein or target molecule, as well as enzyme-linked assays which rely on detecting an enzymatic activity associated with the INDY protein or target molecule.

In addition to cell-based systems, transgenic nonhuman organisms can also be used. A transgenic animal is one in which a heterologous DNA sequence is chromosomally integrated into the germ cells of the animal. The transgeneic animal will also have the transgene integrated into the chromosomes of its somatic cells. Animals of any species, including, but not limited to: mice, rats, rabbits, guinea pigs, pigs, micro-pigs, goats, and non-human primates, e.g., baboons, monkeys, chimpanzees, may be used to generate INDY transgenic animals.

This disclosure further relates to a method of producing transgenic animals, preferably mice, over-expressing Indy, which method comprises the introduction of several copies of a segment comprising at least the polynucleotide sequence encoding SEQ ID NO:2 with a suitable promoter into the cells of an embryo at an early stage. Techniques known in the art may be used to introduce the Indy transgene into animals to produce the founder line of animals. Such techniques include, but are not limited to: pronuclear microinjection (U.S. Pat. No. 4,873,191); retrovirus mediated gene transfer into germ lines (Van der Putten et al., *Proc. Natl. Acad. Sci. USA* 82: 6148–6152, 1985; gene targeting in embryonic stem cells (Thompson et al., *Cell* 56: 313–321, 1989; electroporation of embryos (Lo, *Mol. Cell Biol.* 3: 1803–1814, 1983; and sperm-mediated gene transfer (Lavitrano, et al., *Cell* 57: 717–723, 1989; etc. For a review of such techniques, see Gordon, *Intl. Rev. Cytol.* 115: 171–229, 1989.

Gene targeting by homologous recombination in embryonic stem cells to produce a transgenic animal with a mutation in the Indy gene ("knock-out" mutation) can also be performed. In such so-called "knock-out" animals, there is inactivation of the Indy gene or altered gene expression, such that the animals can be useful to study the function of the Indy gene, thus providing animals models of human disease, which are otherwise not readily available through spontaneous, chemical or irradiation mutagenesis.

A particularly useful transgenic animal in one in which the Indy homolog has been disrupted or knocked out. Analysis of the mouse genome shows only one gene with a very high homology to the fly Indy gene (NaDC-1). A particularly useful transgenic mouse is one in which the Cre-loxP system is used to disrupt exons 5 through 12 of the mNaDC-1 gene to achieve a functionally null allele of mNaDC-1. This mouse model of the Indy mutation will facilitate the understanding of the role of Indy mutations and caloric restriction in life span extension and serve as a step toward the development of pharmaceutical intervention that may mimic caloric restriction in mammals.

Transgenic animals such as mice, for example, may be used as test substrates for the identification of drugs, pharmaceuticals, therapies and interventions that can be used for the treatment of body weight disorders or lifespan extension. For example, any treatments that reverse aspects of body weight disorders such as obesity are considered candidates for human body weight disorder therapeutic treatment.

In another embodiment, treatment of body weight disorders or increasing life span comprises modulating Indy gene expression. A cell or subject can be treated with an agent that modulates Indy gene expression. These agents can be nucleic acid molecules substantially complementary to an Indy gene. Such approaches include oligonucleotide-based therapies such as antisense, ribozymes, triple helices and double stranded interfering RNAs.

Oligonucleotides may be designed to reduce or inhibit mutant target gene activity. Techniques for the production and use of such molecules are well known to those of ordinary skill in the art. Antisense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred. Antisense oligonucleotides are preferably 10 to 50 nucleotides in length, and more preferably 15 to 30 nucleotides in length. An antisense compound is an antisense molecule corresponding to the entire Indy mRNA or a fragment thereof.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules includes one or more sequences complementary to the target gene mRNA, and includes the well known catalytic sequence responsible for mRNA cleavage disclosed, for example, in U.S. Pat. No. 5,093,246. Within the scope of this disclosure are engineered hammerhead motif ribozyme molecules that specifically and efficiently catalyze endonucleolytic cleavage of RNA sequences encoding target gene proteins. Specific ribozyme cleavage sites within any potential RNA target are initially identified by scanning the molecule of interest for ribozyme cleavage sites that include the sequences GUA, GUU, and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules used in triple helix formation for the inhibition of transcription should be single stranded and composed of deoxyribonucleotides. The base composition of these oligonucleotides are designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences targeted for triple helix formation may be increased by creating a "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Double stranded interfering RNA molecules are also useful; see, for example, Fire et al., Nature 391: 860–11, 1998. Such molecules interfere with the expression of a target gene. For example, double stranded RNA molecules can be injected into a target cell or organism to inhibit expression of a target gene and thus the activity of the gene product. Such double stranded RNA molecules can be more effective at inhibiting gene expression than either strand alone.

The antisense, ribozyme, triple helix and/or double stranded interfering RNA molecules described herein may reduce or inhibit the transcription (triple helix) and/or translation (antisense, ribozyme, double stranded interfering RNAs) of mRNA produced by both normal and mutant target gene alleles. If it is desired to retain substantially normal levels of target gene activity, nucleic acid molecules that encode and express target gene polypeptides exhibiting normal activity may be introduced into cells via gene therapy methods that do not contain sequences susceptible to whatever antisense, ribozyme, or triple helix treatments are being utilized. Alternatively, it may be preferable to coadminister normal target gene protein into the cell or tissue in order to maintain the requisite level of cellular or tissue target gene activity.

Antisense RNA and DNA, ribozyme, and triple helix molecules may be prepared by any method known in the art for the synthesis of DNA and RNA molecules. These include techniques for chemically synthesizing oligodeoxyribonucleotides and oligoribonucleotides, for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Various well-known modifications to the DNA molecules may be introduced as a means of increasing intracellular stability and half-life. Possible modifications include but are not limited to the addition of flanking sequences of ribonucleotides or deoxyribonucleotides of the 5' and/or 3' ends of the molecule or the use of phosphorothioate or 2' O-methyl rather than phosphodiesterase linkages within the oligodeoxyribonucleotide backbone.

Modulators of Indy expression are identified in a method wherein a cell is contacted with a candidate compound and the expression of Indy mRNA or protein in the cell is determined. The level of expression of Indy mRNA or protein in the presence of the candidate compound is compared to the level of expression of mRNA or protein in the absence of the candidate compound. The candidate compound can then be identified as a modulator of Indy expression based on this comparison. For example, when expression of Indy mRNA or protein is greater in the presence of the candidate compound than in its absence, the candidate compound is identified as a stimulator of Indy mRNA or protein expression. Alternatively, when expression of Indy mRNA or protein is less in the presence of the candidate compound than in its absence, the candidate compound is identified as an inhibitor of Indy mRNA or protein expression. The level of Indy mRNA or protein expression in the cells can be determined by methods described herein for detecting Indy mRNA or protein.

Delivery of antisense, triplex agents, ribozymes, double stranded interfering RNA and the like can be achieved using a recombinant expression vector such as a chimeric virus or a colloidal dispersion system or by injection. Useful virus vectors include adenovirus, herpes virus, vaccinia, and/or RNA virus such as a retrovirus. The retrovirus can be a derivative of a murine or avian retrovirus such as Moloney murine leukemia virus or Rous sarcoma virus. All of these vectors can transfer or incorporate a gene for a selectable marker so that transduced cells can be identified and generated. The specific nucleotide sequences that can be inserted into the retroviral genome to allow target specific delivery of the retroviral vector containing an antisense oligonucleotide can be determined by one of skill in the art.

Another delivery system for polynucleotides is a colloidal dispersion system. Colloidal dispersion systems include macromolecular complexes, nanocapsules, microspheres, beads, and lipid-based systems including oil-in-water emulsions, micelles, mixed micelles and liposomes. A preferred colloidal delivery system is a liposome, an artificial membrane vesicle useful as in vivo or in vitro delivery vehicles. The composition of a liposome is usually a combination of phospholipids, usually in combination with steroids, particularly cholesterol.

The Indy gene may also be underexpressed, causing metabolic or other disorders in particular. Alternatively, the activity of the Indy gene product(s) may be diminished, leading to the development of disease symptoms. Cellular transporter agonists may be used in such cases to increase nutrient uptake for therapeutic reasons in both humans and animals. Therapeutic uses include, but are not limited to, increasing the rate of growth, the rate of weight gain, and the survival rate of premature offspring, neonates, and the aged; increasing total nutrient uptake in subjects with short bowel syndrome or with surgical resection of the intestine; and improving nutritional status of subjects with eating disorders such as anorexia nervosa and bulimia, subjects with acquired immune deficiency syndrome or other chronic immune deficiency syndromes, individuals with Down's syndrome, and burn victims or other severely traumatized subjects.

Methods whereby the level of Indy gene activity may be increased to levels wherein disease symptoms are ameliorated also include increasing the level of gene activity, for example by either increasing the level of Indy gene present or by increasing the level of gene product which is present.

For example, a target gene protein, at a level sufficient to ameliorate metabolic imbalance symptoms, may be administered to a patient exhibiting such symptoms. One of skill in the art will readily know how to determine the concentration of effective, non-toxic doses of the normal target gene protein. Additionally, RNA sequences encoding target gene protein may be directly administered to a patient exhibiting disease symptoms, at a concentration sufficient to produce a level of target gene protein such that the disease symptoms are ameliorated. Administration may be by a method effective to achieve intracellular administration of compounds, such as, for example, liposome administration. The RNA molecules may be produced, for example, by recombinant techniques such as those described above.

Further, patients may be treated by gene replacement therapy. One or more copies of a normal target gene, or a portion of the gene that directs the production of a normal target gene protein with target gene function, may be inserted into cells using vectors that include, but are not limited to adenovirus, adenoma-associated virus, and retrovirus vectors, in addition to other particles that introduce DNA into cells, such as liposomes. Additionally, techniques such as those described above may be utilized for the introduction of normal target gene sequences into human cells.

Cells, preferably, autologous cells, containing normal target gene expressing gene sequences may then be introduced or reintroduced into the patient at positions which allow for the amelioration of metabolic disease symptoms. Such cell replacement techniques may be preferred, for example, when the target gene product is a secreted, extracellular gene product.

In instances where the target gene protein is extracellular, or is a transmembrane protein, any of the administration techniques described, below which are appropriate for peptide administration may be utilized to effectively administer inhibitory target gene antibodies to their site of action.

The identified compounds that inhibit target gene expression, synthesis and/or activity can be administered to a patient at therapeutically effective doses to treat or ameliorate obesity, metabolic disorders, or the symptoms of aging. A therapeutically effective dose refers to that amount of the compound sufficient to result in amelioration of symptoms of obesity, metabolic disorders, or the symptoms of aging.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p- hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The discovery of the Indy gene provides a therapeutic target for control of weight gain and extension of life span. The similarity of INDY to cellular transporters and the localization of INDY suggest that it acts through caloric restriction. Unlike other genes previously associated with life-extension in metazoans, Indy appears to be directly involved in intermediary metabolism and thus represents a new class of longevity genes.

While it is presently hypothesized that Indy and its homologs mediate the biological events of extended life span and/or caloric restriction, all embodiments of this disclosure are equally applicable to any gene product and/or lack of a gene product from the mutations of the Indy gene as described above.

All references cited herein are incorporated by reference in their entirety. The invention is illustrated by the following non-limiting examples.

EXAMPLE 1

Identification of Indy Mutants

In order to identify *Drosophila* strains with extended life spans, *Drosophila* enhancer-trap lines were studied. An enhancer-trap *Drosophila* line is one in which a P-element has been inserted. A *Drosophila* P-element is a transposon that provides a vector for the introduction of a wide variety of genes into the *Drosophila* germ line. A transposon is a DNA element that promotes its own transposition between different genetic loci. A wild-type *Drosophila* P-element is 2.9 kb in length and can include the gene for transposase, an enzyme that facilitates transposition. The enhancer-trap P-element cannot mobilize itself, but requires the presence of transposase from another source. The enhancer-trap P-element is a modified P-element which is about 10 kb and contains such DNA sequences as the P-element long terminal like repeats, the gene for bacterial lacZ, the white minigene which gives the fly a pigmented eye, a region for plasmid rescue, an origin of replication and ampicillin resistance. The P-element also contains a minimal promoter region, which is insufficient itself to induce transcription, but can be transcribed if inserted in a region of the *Drosophila* genome that contains an enhancer. Because the P-element contains the lacZ gene, the activity of the reporter gene can be assayed using standard β-galactosidase assays. The P-elements thus insert somewhat randomly into the *Drosophila* germ line, and may interfere with gene expression and essentially become mutants that can be assayed for a particular phenotype. The *Drosophila* enhancer lines used are described in Boynton and Tully, *Genetics* 131: 655–72, 1992.

Figure 4:
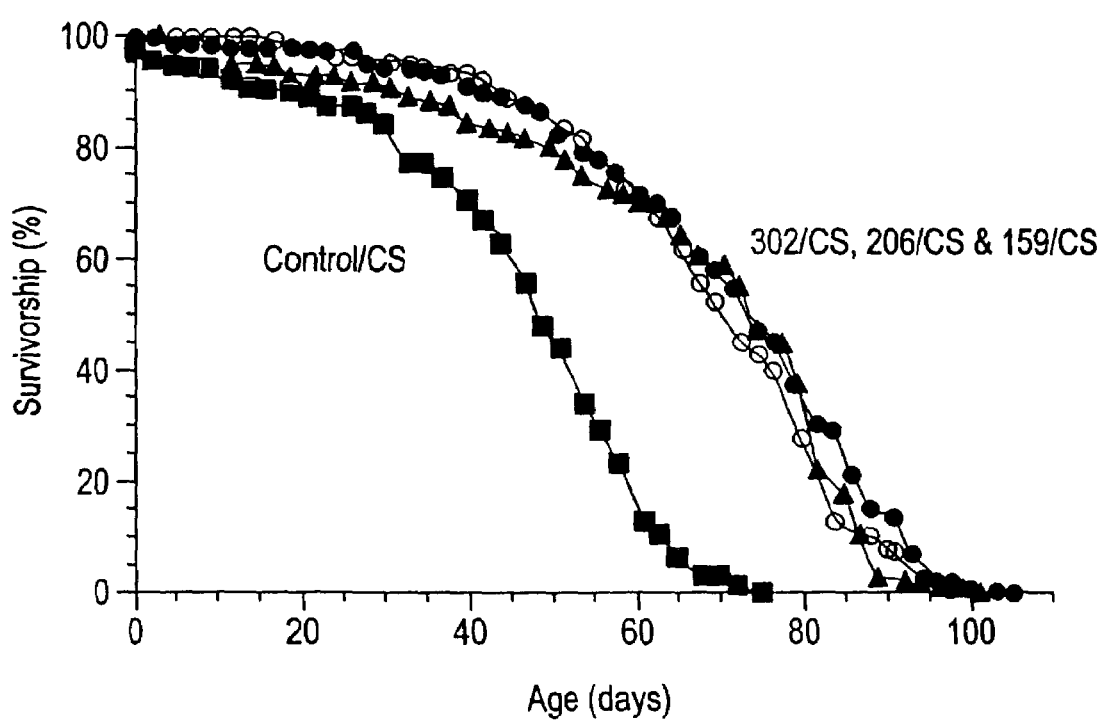
FIG. 4 shows life-span extension in Indy mutants, wherein survival curves of males heterozygous for three different Indy mutations and an enhancer-trap control are compared. All flies were tested as heterozygotes over a wildtype Canton-S strain. The Indy mutants are Indy302 (open circle), Indy206 (closed circle), and Indy159 (closed triangle). The control (closed box) is one of four other enhancer-trap control lines from the same mutagenesis that generated Indy302 and Indy206 tested as a heterozygote over Canton-S. A similar control survival curve was found for a control from the mutagenesis that gave rise to Indy159.

In the search for long-lived *Drosophila* mutants, it was observed that two fly lines, 206 and 302, showed a near doubling of mean life-span (from 37 to 70 days) and a 50% increase in maximal life-span (FIG. 4). The mean 25° C. life spans of controls were 37 days, while the mean life spans for Indy206, Indy302, and Indy159 were 71, 69, and 69 days respectively. Indy206, Indy302, and Indy159 extended mean life span by 92%, 87%, and 87% respectively. Extension of 1% maximal life span of these Indy mutants was greater than 45%. At 18° C., the increase in mean life span conferred by Indy mutations approaches 100% while the increase in 1% maximum life span approaches 50%. Flies were maintained in a humidified, temperature controlled environmental chamber at 25° C., transferred to fresh food vials and scored for survival every 2 to 3 days. Each survivorship curve represents data from over 300 male flies. A total of 5430 male and female Indy heterozygote flies were tested.

The increase in life span occurred only in heterozygotes, that is flies with only one copy of the enhancer-trap chromosome and a copy of a normal Indy gene. Chromosomal in situ hybridization revealed that the P-element in both the 206 and 302 cell lines was inserted at the same cytological location. Genomic DNA flanking the site of insertion in the 206 and 302 cell lines was obtained by plasmid rescue and sequenced. The insertion sites in the 206 and 302 enhancer trap cell lines were 5753 base pairs from each other and were in the same gene, which has been named Indy (for I'm not dead yet). The Indy cDNA is SEQ ID NO:1.

EXAMPLE 2

Identification of the Indy Gene

Information on the chromosomal location of Indy was used to identify additional mutations in the Indy gene from other laboratories. Several candidate lines with P-element insertions in the same cytogenic location as Indy were examined. A third enhancer-trap line, the 159 fly line, with a P-element inserted 734 base pairs from the site of the 206 insertion was identified. As a heterozygote, this 159 fly line showed a similar extension in life span to the other Indy insertions (FIG. 4). Two further P-element insertions in Indy were obtained through site-selected mutagenesis of the Indy locus. In a polymerase chain reaction-based screen of 10,000 mutagenized third chromosomes, two new insertions into the Indy locus, lines 92 and 265, were identified. Flies heterozygous for either the 92 or 265 allele showed extension of life span similar to that of the original selected mutants. The accession number for the Indy cDNA is AF217399 and the flybase number is CG3979.

The genomic organization of the Indy locus with the insertion sites of all five P-element alleles is shown in FIG. 3. The organization of the Indy transcription unit is shown, with the "atg" initiation codon and "tag" stop codon noted. Solid black boxes represent the conserved AntC and Fas1 nucleotide sequences found 5' of the transcriptional start site of the Indy gene and that are thought to be involved in regulation of gene expression. AntC has a high level of homology to the 5' region of the Antennapedia gene. Fas1 has a high level of sequence homology to the 5' region of the Fasiculin 1 gene. The gray rectangle is the sequence of the conserved Hoppel transposable element found in the first intron of the Indy gene. Hoppel is another type of transposable element in Drosophila and this element is found in the first intron of the Indy gene is wild type flies. The original enhancer-trap lines are shown as PlacW302, PlacW206 and PlacW159. The orientation of the insertion is indicated 5' to 3' by the black arrow. Two of the original lines are insertions in the Hoppel element in the first intron just upstream of the coding region (206 and 159). The third original Indy stock (302) has its insertion just upstream of the transcriptional start site. The Indy mutants generated by site-selected mutagenesis are indicated as Birmingham-2 P-element insertions PBm92 and PBm265. The PlacW insertion is not drawn to scale.

Figure 5:
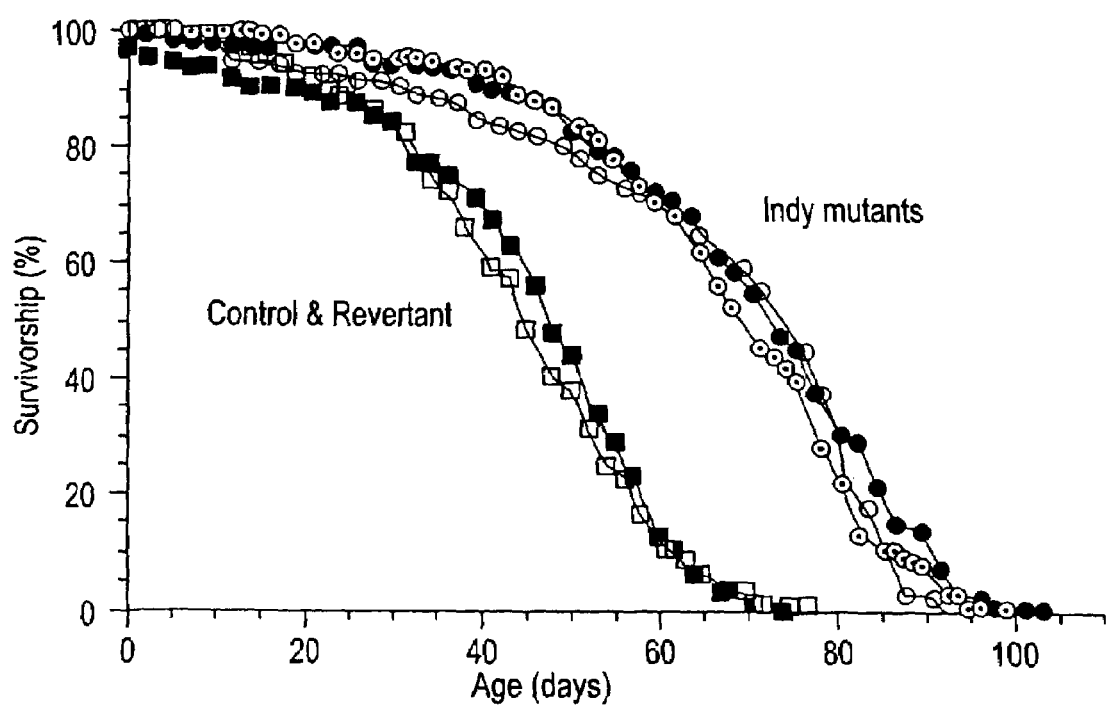
FIG. 5 shows the reversion of life-span extension upon P-element removal. Survival curves of males heterozygous for three different Indy mutations, a precise excision of the P-element from Indy302 (revertant), and an enhancer-trap control are shown. The Indy mutants are Indy302 (open circle), Indy206 (closed circle), and Indy159 (closed triangle). The excision line (revertant-open box) is one of four exact excisions (sequence confirmed) of the P-element obtained by mobilizing the P-element from either the Indy302 or Indy206 line. The control (closed box) is one of four other enhancer-trap control lines from the same mutagenesis that generated Indy302 and Indy206 tested as a heterozygote over Canton-S.

To confirm that the P-element insertion in Indy caused the observed life-span extension, the P-element was remobilized and excised from the 206 and 302 lines. Four independent lines of flies, shown by sequence analysis to carry exact excisions, reverted to normal lifespan (FIG. 5). A nonexcision control line isolated at the same time which passed through the same genetic background as the excision lines remained long-lived.

EXAMPLE 3

Confirmation that the Indy Mutations Have a Positive Effect on Life Span

Figure 6:
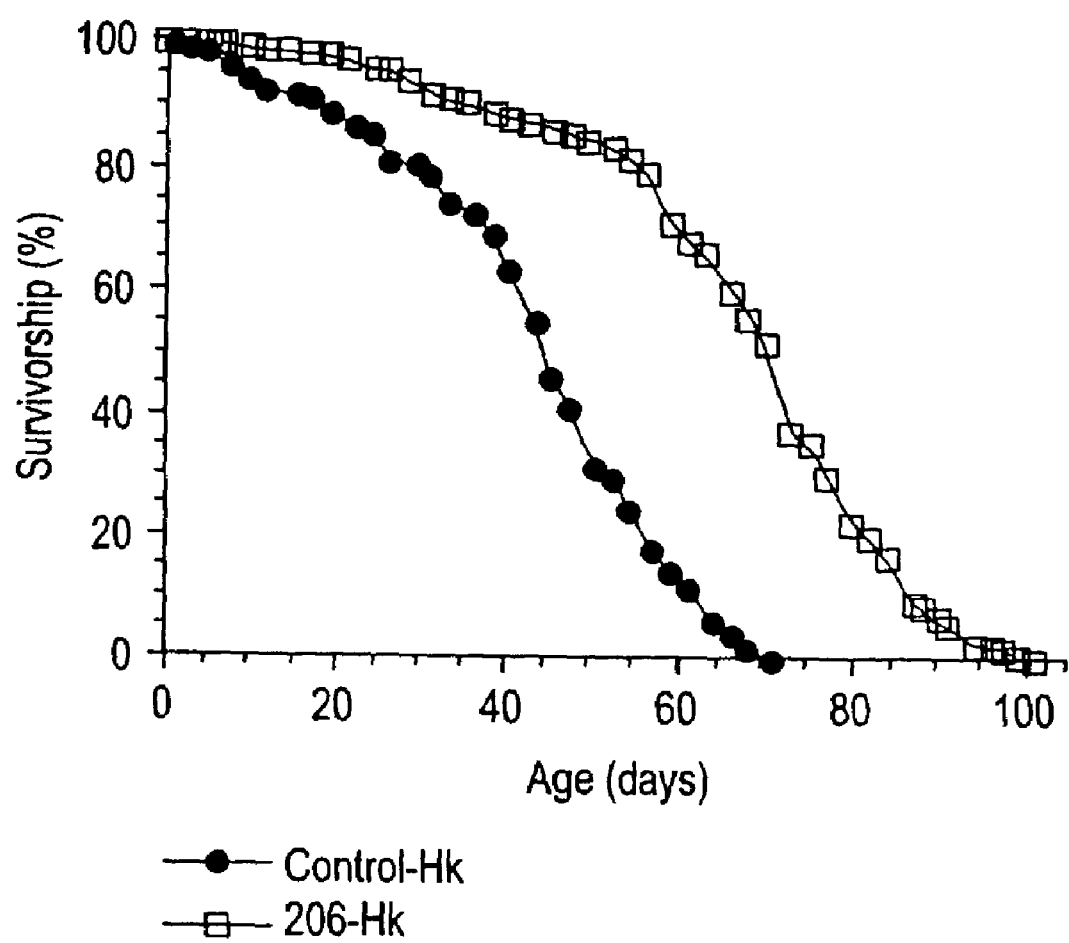
FIG. 6 shows the survival curve for a control hyperkinetic line (closed circles) and a hyperkinetic line crossed with the Indy206 mutant line (open squares).
Figure 7:
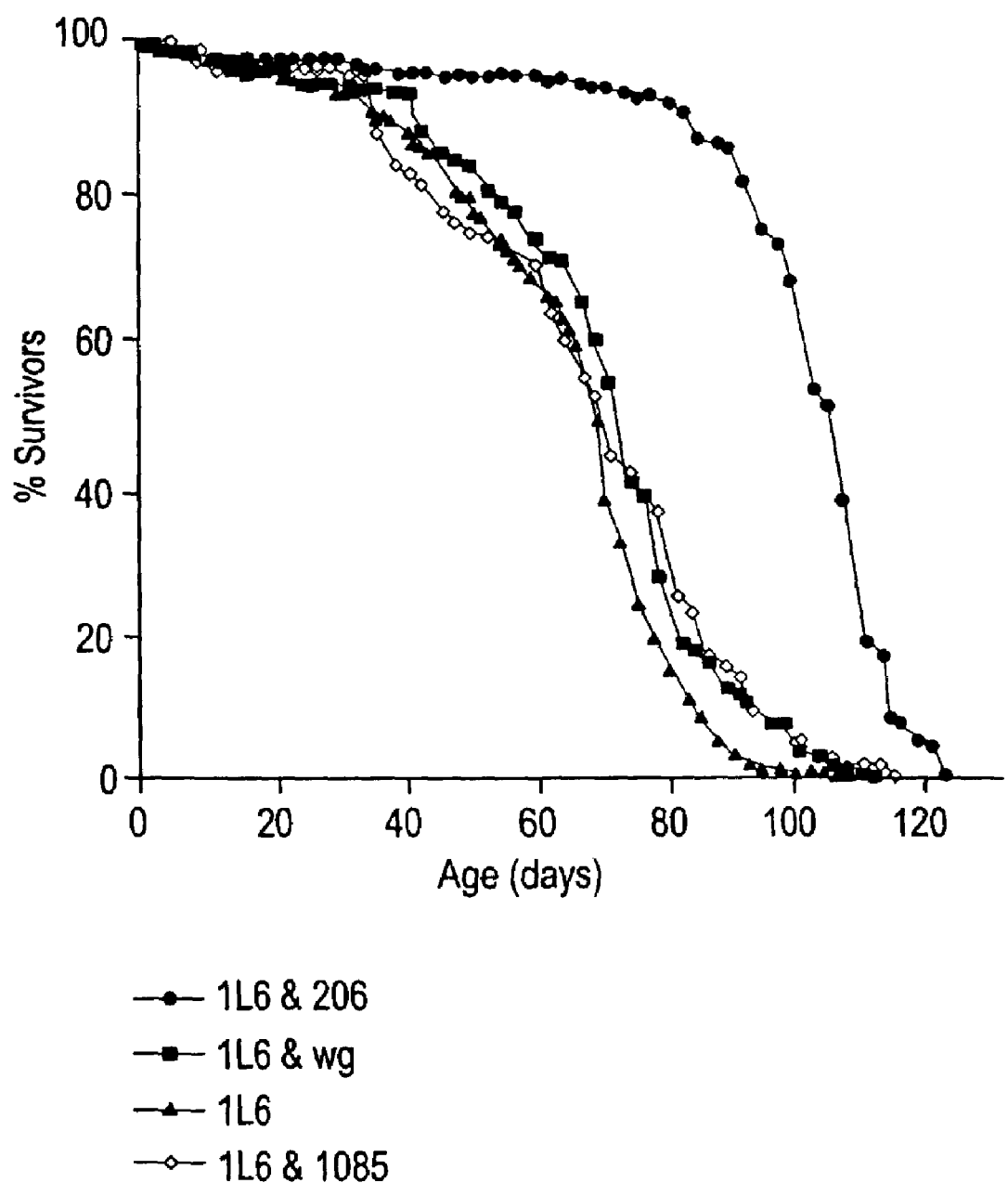
FIG. 7 shows the survival curve for the luckinbill I16 line (triangle), the luckinbill I1-6 line crossed with the 1085 line as a control (diamond), the luckinbill I1-6 line crossed with the wg line as a control (square) and the luckinbill I1-6 line crossed with Indy line 206 (circle).

To exclude the possibility that the extended life span of the Indy mutants was due to the rescue of uncharacterized deleterious mutations accumulating in the wild-type Canton-S stock, the Indy mutation was crossed into several different genetic backgrounds distinct from the Canton-S stock. The stocks tested included the Hyperkinetic, Shaker, and drop dead stocks, each of which was isolated from other laboratory stocks over 25 to 30 years ago. Also tested was a long-lived Luckinbill laboratory selected line. In all cases, there was an extension of life span. For Hyperkinetic, Shaker and drop-dead, the mean life span was extended 40–80% (FIG. 6). For the Luckinbill line, life span was additionally extended by 15% (FIG. 7). These data indicate that the mechanism by which Indy mutations extend life span is a positive effect of the mutation and not simply the effect of rescuing deleterious mutations. The smaller increase in life-span associated with the laboratory-selected long-lived lines provides additional evidence that the mechanisms by which Indy acts to increase life-span may represent physiological systems already partially optimized by laboratory selection.

Figure 8:
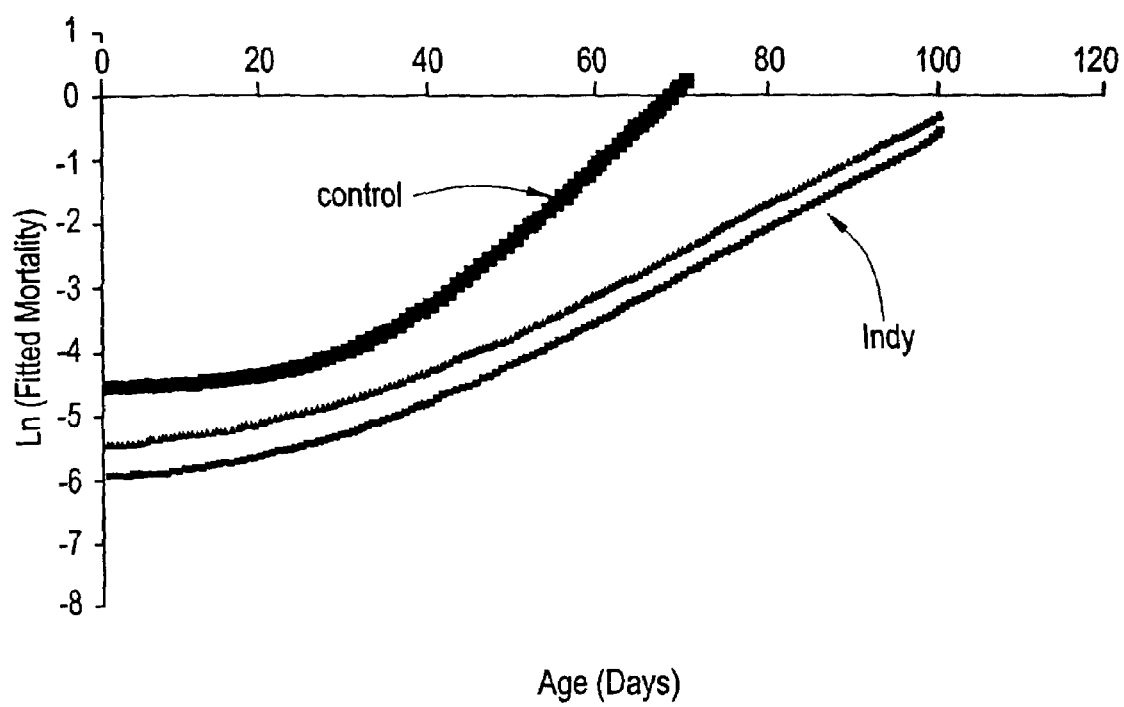
FIG. 8 shows the rate of aging for a normal fly (squares) and Indy heterozygous flies (triangles and circles).

Life span can be increased with or without a change in the rate of aging. Treatments such as lowering growth temperature and caloric restriction decrease the rate of aging. In most long-lived Drosophila mutants that have been characterized, the aging process is simply delayed without a change in the rate of aging. Indy heterozygous mutants, however, show a significant decrease in the rate of aging (FIG. 8). Indy is thus the first long-lived Drosophila mutant to show a change in the rate of aging rather than simply a delay in the initiation of the aging process.

EXAMPLE 4

Characterization of the Indy Gene Product

Figure 9:
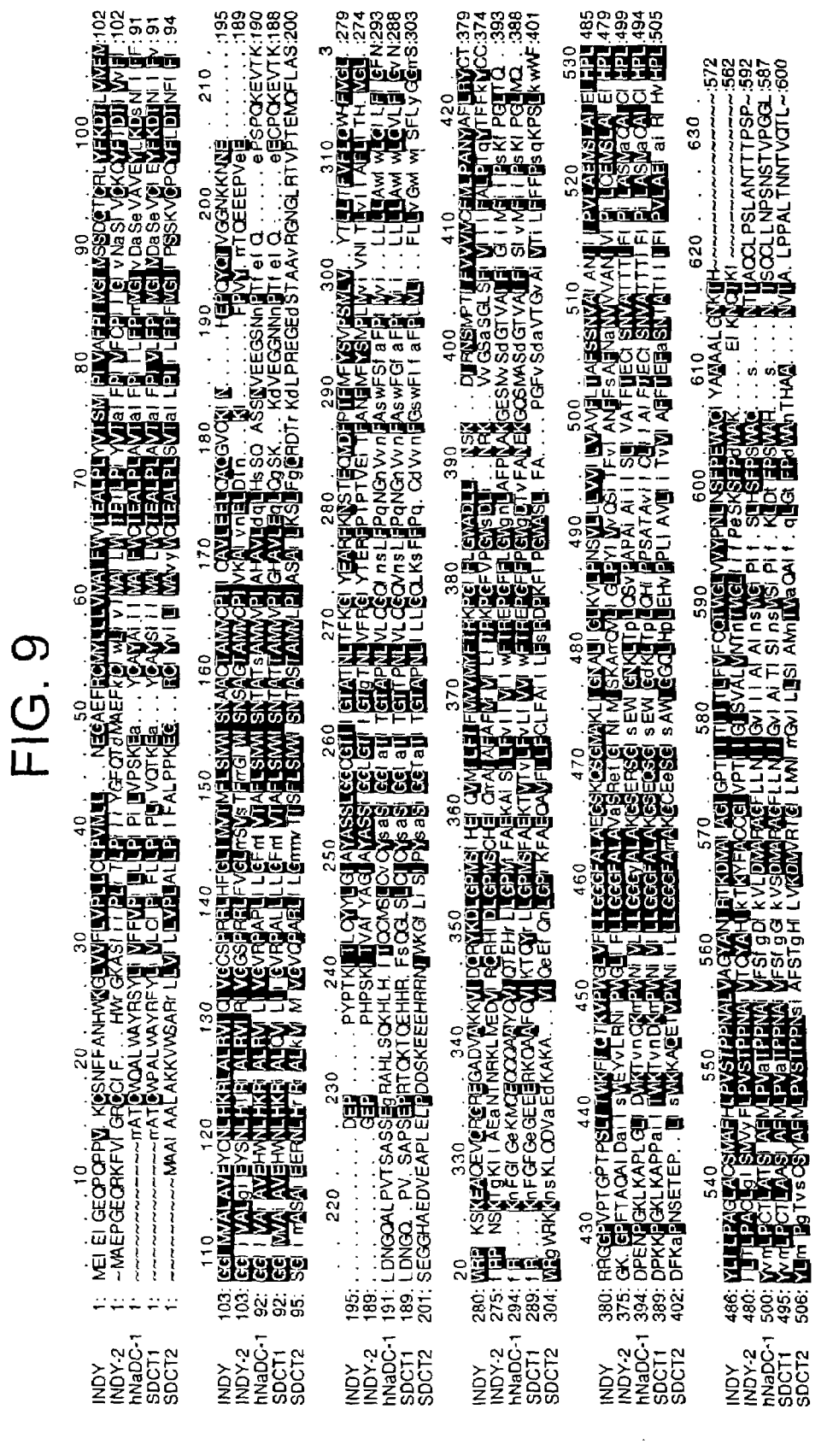
Figure 10:
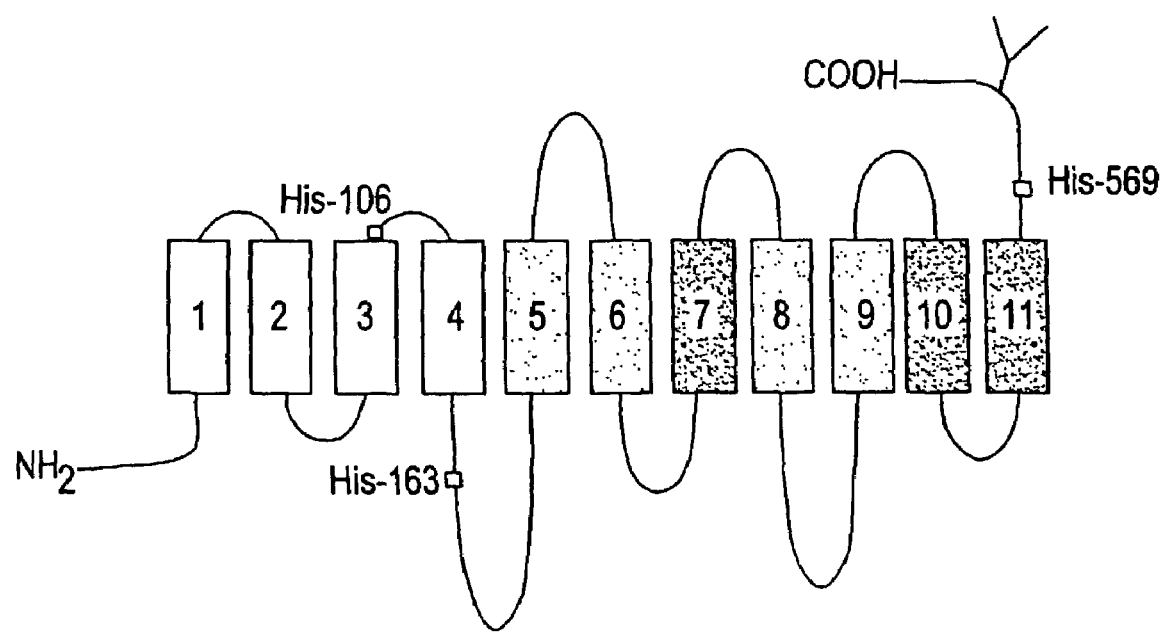
FIG. 10 shows a schematic of the structure of a sodium dicarboxylate cotransporter. The model shows 11 transmembrane domains, an intracellular amino terminal domain, and a carboxyl terminal extracellular domain.
Figure 11A:
FIG. 11 shows the expression of Indy in adult flies. Whole mount X-gal staining shows nuclear localization of β-gal in cells from lines carrying an enhancer-trap insert in the Indy gene—Indy302, Indy206, and Indy159. Expression is seen in oenocytes (A, B) and gut (C, D). Low power views of oenocytes in the (v) ventral and (d) dorsal abdominal segments are shown in (A). A high power view of dorsal midline oenocytes is shown in (B). Panel (D) shows a 5 µm section showing X-gal staining within the cells of the gut. After whole mount X-gal staining, the tissue in (D) was postfixed in 6.25% glutaraldehyde, embedded in paraffin, and then sectioned. The scale bar in A, B, and C is 100 µm. In (D) the scale bar is 10 µm.
Figure 11B:
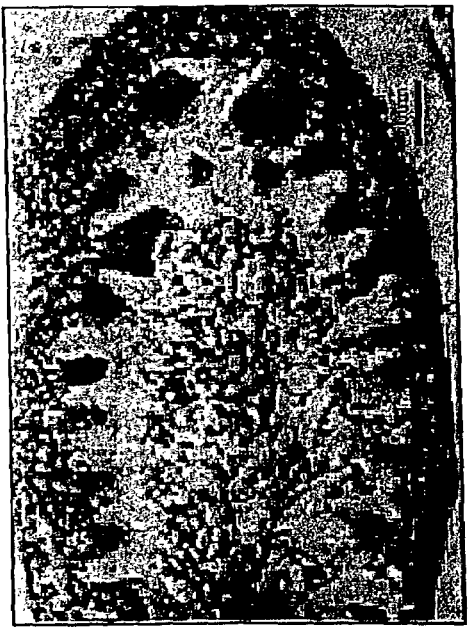
Figure 11C:
Figure 11D:
Figure 12A:
FIG. 12 shows the subcellular localization of INDY using an anti-INDY antibody. INDY is localized to the plasma membrane of midgut epithelial cells, fat body cells, and oenocytes (Dark staining in panels A, B, and D. Panel C is an immunofluoresence image of the midgut showing staining expected from basolateral proteins. Dark staining shows antibody localization to the plasma membranes of midgut (dark staining) localized to the basolateral aspects of the midgut.
Figure 12B:
Figure 12C:
Figure 12D:
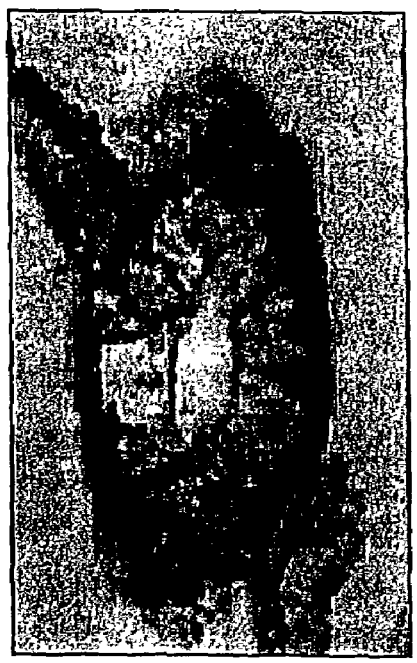

Genomic and cDNA sequences of the Indy gene predicted a 572-amino acid protein (Seq. ID NO. 2) with 34% identity and 50% similarity to human, mouse and rat renal sodium dicarboxylate cotransporters (FIG. 9). The accession number for the Indy polypeptide is AE003519. Mammalian dicarboxylate cotransporters are membrane proteins responsible for the uptake or re-uptake of di- and tricarboxylic acid Krebs cycle intermediates such as succinate, citrate, and alpha-ketoglutarate. A schematic of a dicarboxylate cotransporter is shown in FIG. 10. They are found in a variety of tissues, including brush border cells of the small intestine, colon and placenta; the basolateral membrane of perivenous cells in the liver; and epithelial cells of the renal proximal tubule and the brain. Dicarboxylate cotransporters are also found in the placenta and brain of mammals.

EXAMPLE 5

Localization of the Indy Gene Product

The P-element insertion encodes a reporter protein β-galactosidase (β-gal), which allows localization of the Indy gene message. Expression of β-gal was visualized by X-gal staining. Indy has an identical pattern of expression in the 206, 302 and 159 enhancer-trap lines despite the P-elements being almost 6.5 kb away from each other in the three lines. In adult flies, Indy is expressed in the fat body, midgut, and oenocytes (FIG. 11). These organs are thought to be the primary sites of intermediary metabolism, absorption, and metabolic storage in Drosophila. The fat body is involved in the metabolism and storage of fat, glycogen, and protein and is most often compared to the liver in vertebrates. Indy was also expressed at lower levels in the halteres; portions of the alimentary canals, including the procardia and restricted regions of the esophagus and hindgut; and the base of the legs. These are regions that have been identified as storage deposits for glycogen. Finally, Indy was expressed in a subset of cells in the third segment of the antennae.

The localization of INDY was also determined using staining with an anti-INDY antibody. Two INDY peptides were used to generate antibodies in a rabbit: EPQ YQI VGG NKK NNE DE (amino acid residues 181–197 of SEQ ID NO:2) and RPK SKE AQE VQR GRE GAD VA (amino acid residues 281–300 of SEQ ID NO:2).

The synthesis of an immunogenic peptide is followed by injection into two New Zealand white rabbits. Subsequent boosts and bleeds are taken according to our ten-week protocol. We received 5 mgs of peptide, aliquots of prebleeds., roughly 80 ml of crude sera from each of the two rabbits, and ELISA titration data. INDY staining was visualized by using an anti-rabbit secondary antibody coupled to horseradish peroxidase (HRP) and then reacted with DAB to visualize INDY staining as a brown precipitate (FIG. 12). The use of the antibodies demonstrated that the location of the INDY protein is primarily the plasma membrane of the cells in which it is expressed. More specifically, in the midgut, INDY is expressed prominently on the basolateral portion of the epithelium, and possibly the apical region.

EXAMPLE 6

Biological Function of Indy

To confirm that INDY is a transporter, the Indy mRNA was injected into *Xenopus laevis* oocytes. Stage V and VI oocytes from *Xenopus laevis* were dissected and defoliculated. The oocytes were injected with 25–50 ng of Indy mRNA 1 day after isolation. Nutrient uptake was measured 6 to 7 days later. The oocytes were maintained at 18° C. in Barth's solution containing 50 mg/ml gentamycin sulfate, 2.5 mM sodium pyruvate, and 5% heat-inactivated horse serum (Coady et al., *Arch. Biochem. Biophys.* 283: 130–134, 1990; Pajor and Wright, *J. Biol. Chem* 26:, 3557–3560, 1992).

Transport measurements were performed as in Pajor, *J. Biol. Chem.* 270: 5779–5785, 1995. Groups of oocytes were first washed in choline buffer to remove the serum. Transport was initiated by adding 0.4 ml of [$^{14}$C] succinate or [$^{14}$C] citrate in buffer A. Buffer A comprises 100 mM NaCl, 2 mM KCl, 1 mM $MgCl_2$, and 10 mM HEPES-Tris (pH 7.5). Buffer B is the same as buffer A except the NaCl is replaced by 100 mM choline Cl. For other cation replacement studies, the sodium was replaced by equimolar amounts of the other cations, as their chloride salts. At the completion of the transport time, the nutrient uptake was stopped with 4 washes of 4 ml of ice-cold buffer B. To count the amount of [$^{14}$C] taken up by the oocyte, each oocyte was dissolved in 0.5 ml of 10% SDS, and the [$^{14}$C] assayed by scintillation counting.

Figure 13:
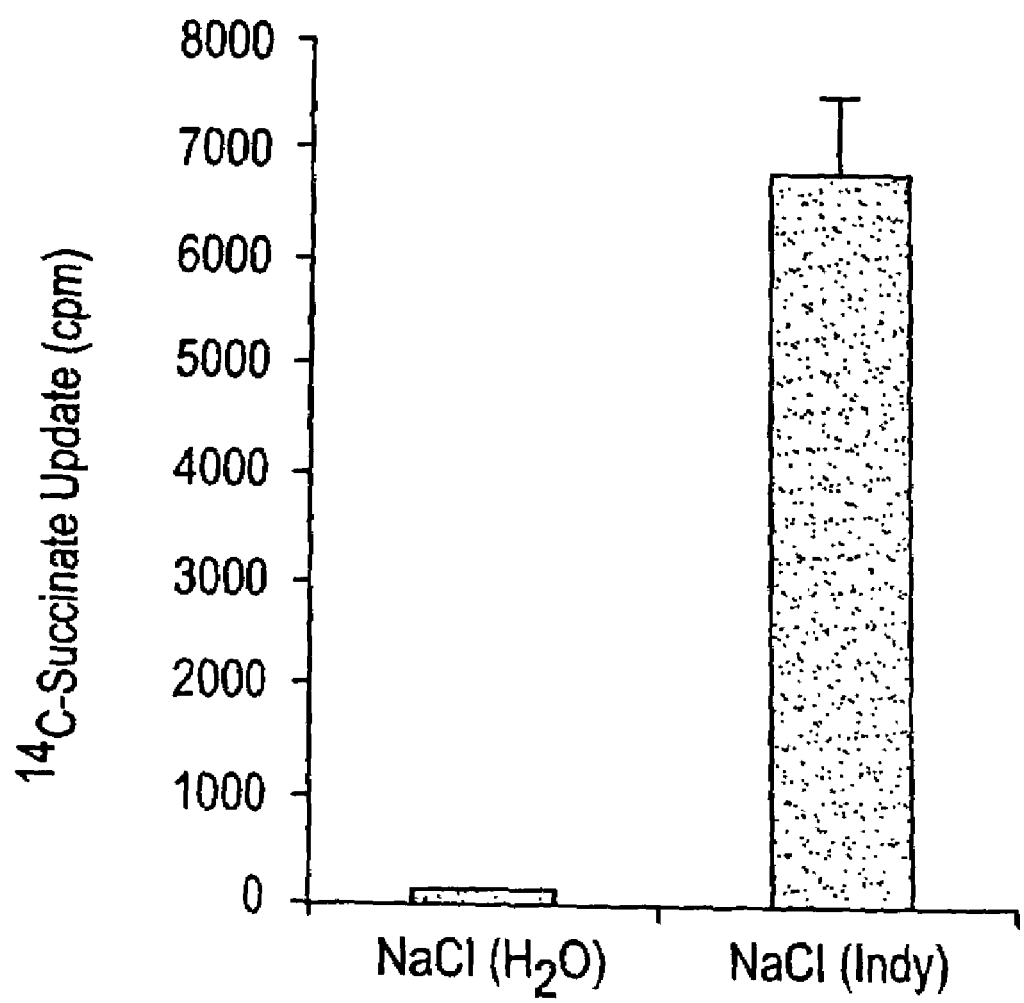
FIG. 13 shows the uptake of [$^{14}$C] succinate in the presence of NaCl by Xenopus oocytes injected with the Indy mRNA or an $H_2O$ control.

When Indy mRNA was injected into *Xenopus* oocytes, greater than a 100-fold increase was observed in the uptake of [$^{14}$C] succinate as compared to a control $H_2O$ injected oocyte (FIG. 13). This increase in succinate transport is comparable to that observed for sodium dicarboxylate cotransporters such as the rat renal transporter.

Figure 14:
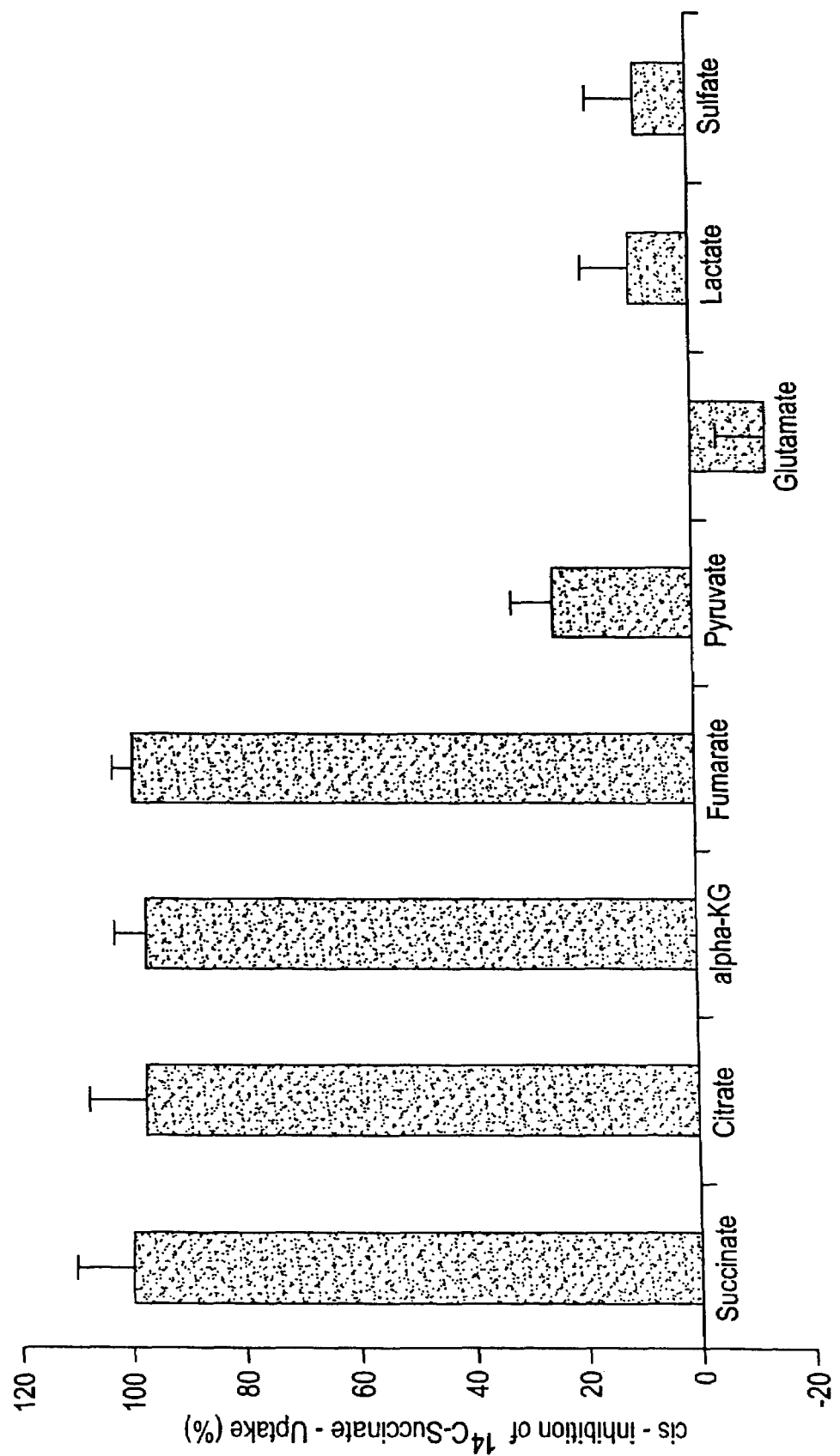
FIG. 14 shows the inhibition of succinate uptake in Xenopus oocytes expressing the Indy mRNA in the presence of succinate, citrate, alpha-ketoglutarate, fumarate, pyruvate, glutamate, lactate, or sulfate.

Studies of sodium dicarboxylate cotransporters have indicated a broad range of specificity for di- and tri-carboxylic acids and the exclusion of monocarboxylic acids. The transport specificity of Indy was thus determined as the ability of various compounds to inhibit the uptake of [$^{14}$C] succinate. The test inhibitors were added at a concentration of 1 mM, approximately a 100-fold excess of inhibitor. As seen in FIG. 14, succinate, citrate, alpha-ketoglutarate, and fumarate inhibit succinate uptake nearly 100%. There is little inhibition of succinate transport by pyruvate, glutamate, lactate, or sulfate.

Figure 15:
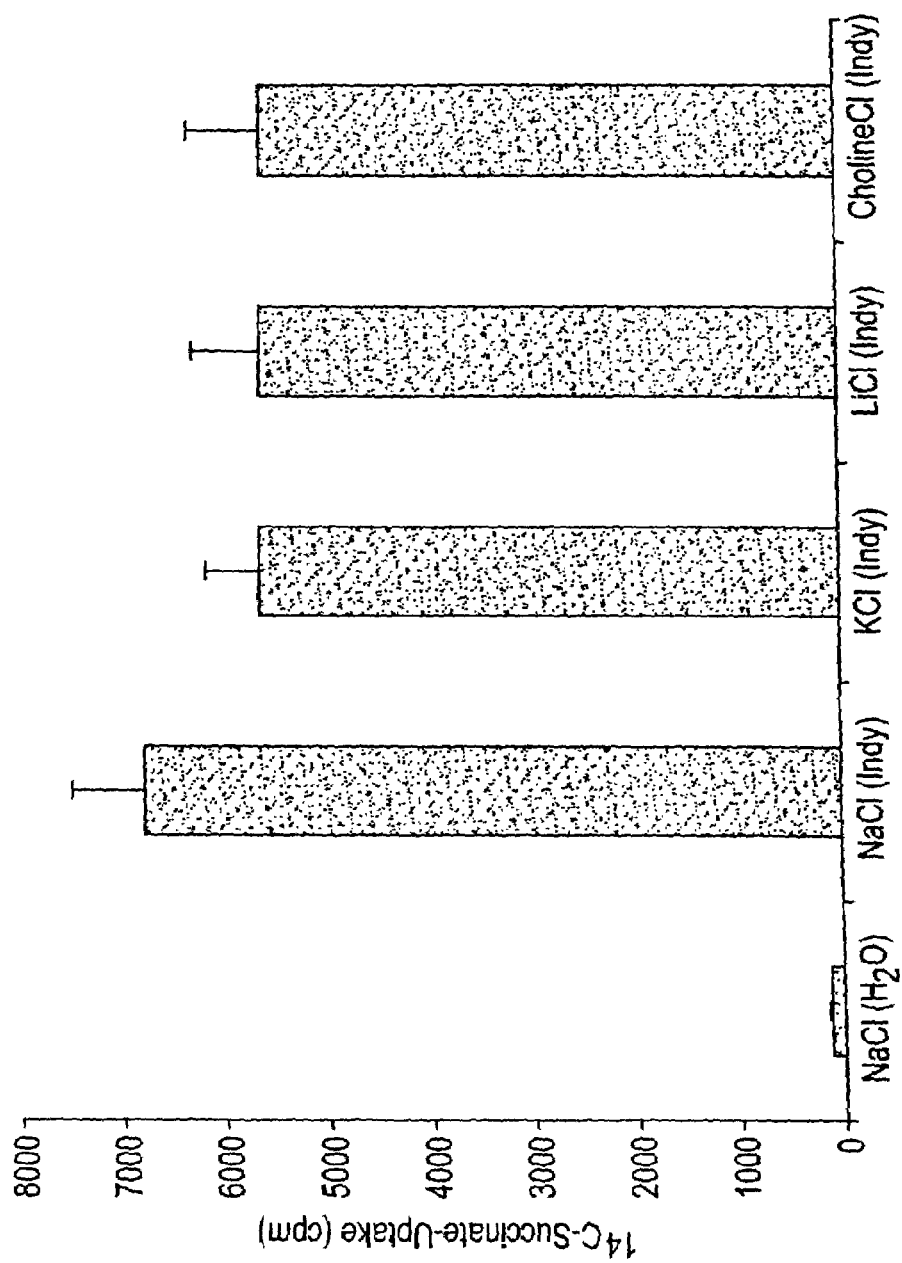
FIG. 15 shows the cation independence of succinate uptake in Xenopus oocytes expressing the Indy mRNA. The [$^{14}$C] succinate uptake is measured in the presence of NaCl, KCl, LiCl and CholineCl. A control in which oocytes were injected with $H_2O$ shows no succinate uptake.

One feature of the sodium dicarboxylate cotransporters that has been studied is cation-dependence of the transport. Transport of succinate in the rabbit renal sodium dicarboxylate cotransporter is dependent on a cation, preferably sodium (Pajor et al., *J. Biol. Chem.* 273: 18923–18929, 1998). Lithium can support transport in the absence of sodium, but becomes an inhibitor in the presence of sodium. It is speculated that lithium has a high affinity for one of the three postulated sodium binding sites in the cotranporter. In contrast to lithium, choline is a potent inhibitor of succinate transport suggesting that the rabbit renal dicarboxylate cotransporter is a true transporter requiring cation cotransport. The cation specificity of Indy was thus examined. In contrast to the sodium dicarboxylate cotransporters, Indy demonstrates similar transport in the presence of sodium, lithium, potassium, and choline (FIG. 15). This result strongly suggests that Indy is a transporter rather than a cotransporter. Thus Indy may represent a new class of cation-independent dicarboxylate transporters.

Figure 16:
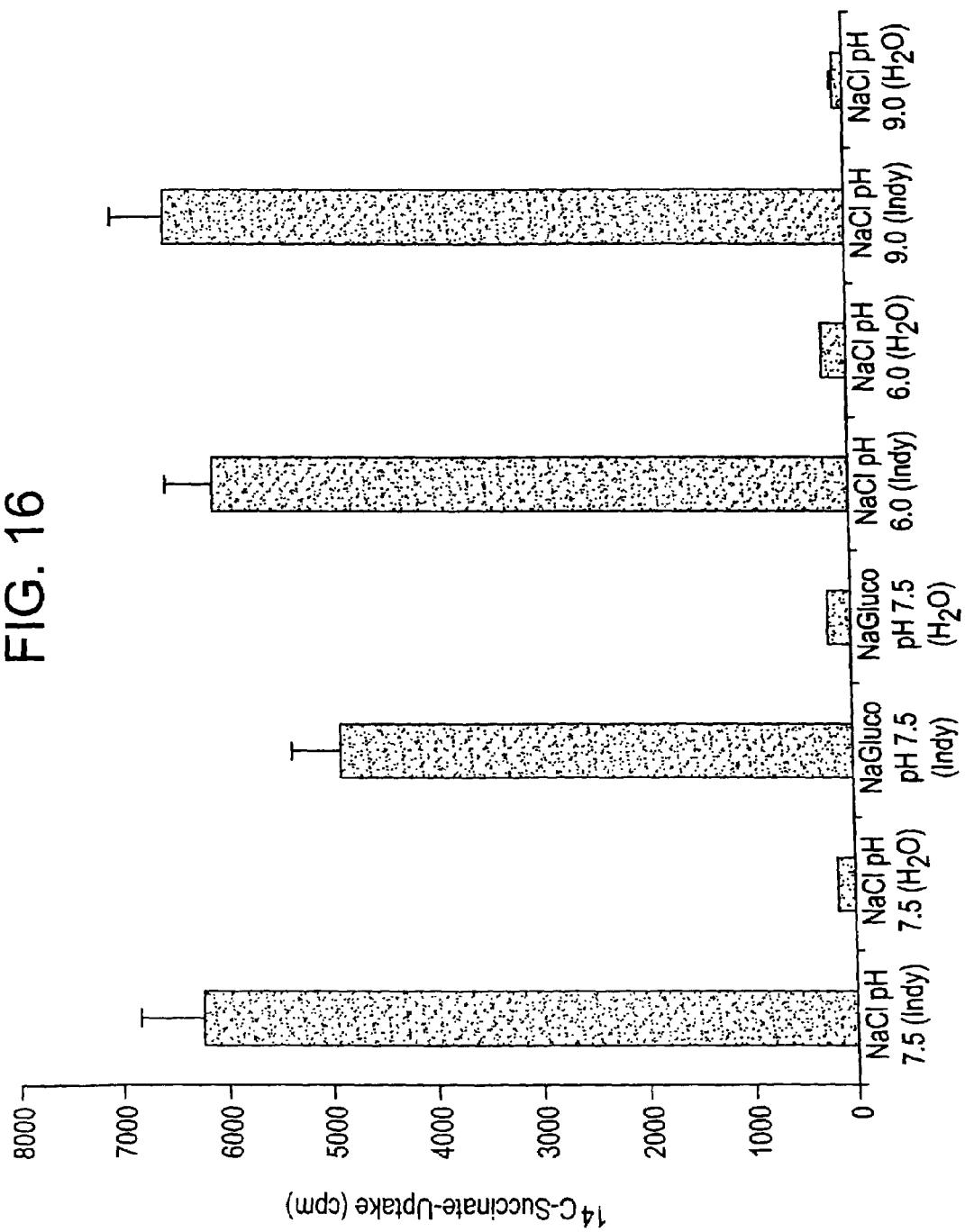
FIG. 16 shows the pH-independence of [$^{14}$C] succinate uptake in Xenopus oocytes injected with $H_2O$ or the Indy mRNA in the presence of NaCl or Na gluconate (NaGluco).

The pH-dependence of succinate transport was also determined. As with the sodium dicarboxylate cotransporters, succinate transport by INDY shows very little dependence on pH and appears not to be using protons as a cotransporter (FIG. 16).

Figure 17:
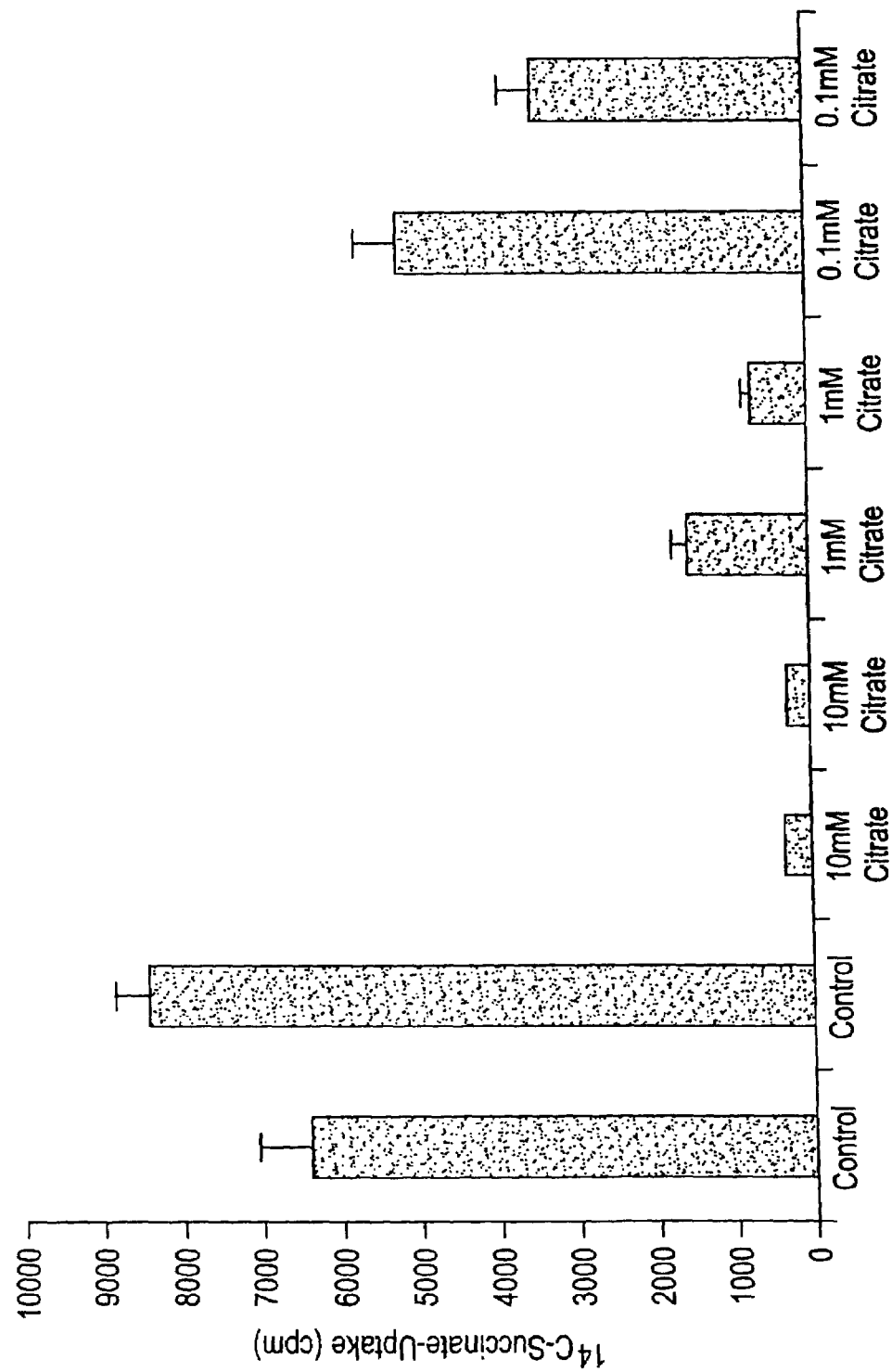
FIG. 17 shows the citrate inhibition of [$^{14}$C] succinate uptake in Xenopus oocytes injected with $H_2O$ or the Indy mRNA. Citrate is added at 10 mM, 1 mM and 0.1 mM concentrations.

The relative affinity of INDY for succinate and citrate was determined by adding a constant amount of [$^{14}$C] succinate and increasing concentrations of citrate to oocytes expressing INDY. As seen in FIG. 17, citrate at 10 mM completely inhibits succinate uptake, citrate at 1 mM inhibits succinate uptake by about 90% and 0.1 mM citrate inhibits succinate uptake by about 50%.

Figure 18:
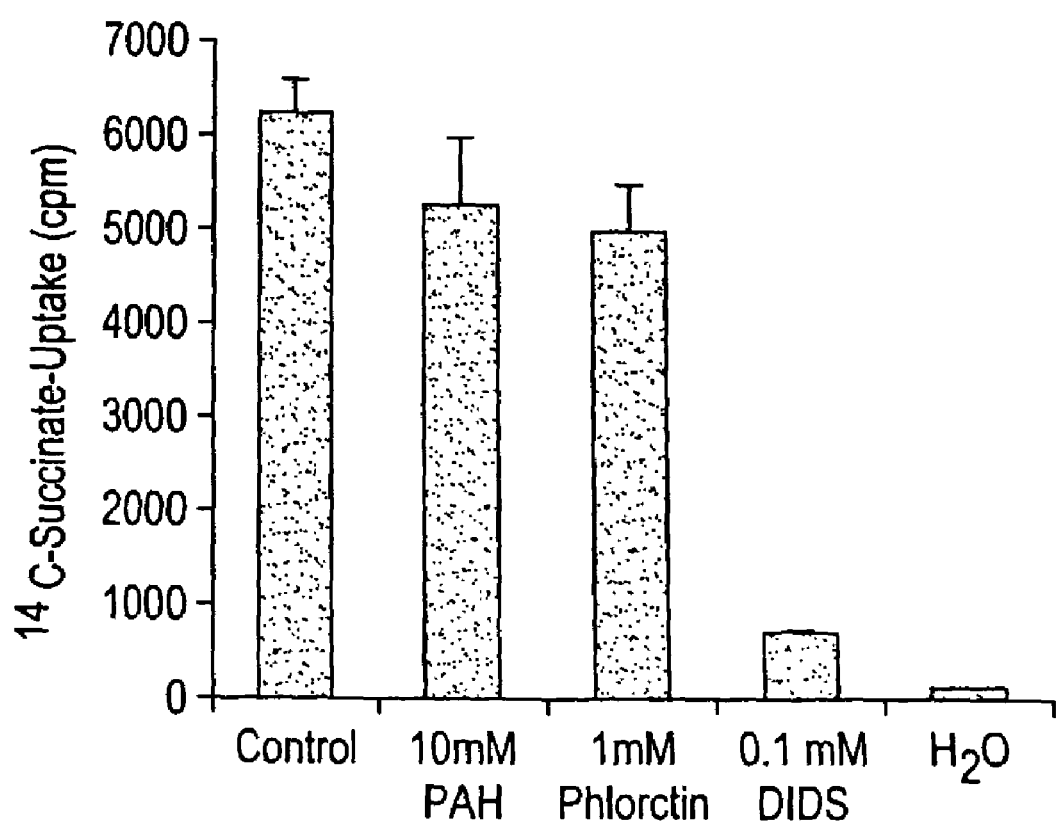
FIG. 18 shows the effect of ion channel inhibitors on [$^{14}$C] succinate uptake in Xenopus oocytes injected with $H_2O$ or the Indy mRNA. The inhibitors used are 10 mM p-aminohippuric Acid (PAH), 1 mM phloretin and 0.1 mM 4,4'-diisothyocyanostilbene-2,2'-disulfonic acid (DIDS).

To further characterize INDY, inhibitors of transport were added to the Indy oocyte system. P-aminohippuric Acid (PAH) is a reference compound used to study transport mechanisms. 4,4'-Diisothyocyanostilbene-2,2'-disulfonic acid (DIDS) is a specific inhibitor of channels. Phloretin is an inhibitor of channels that is known to block protein kinase C. Both PAH and phloretin have no effect on succinate transport while DIDS inhibits succinate transport by 80% (FIG. 18). The lack of inhibition by phloretin is interesting because phloretin has been shown to inhibit both inward and outward currents in sodium-dependent transport in the rat sodium dicarboxylate cotransporter (Chen et al., *J. Biol. Chem.* 273: 20972–20981, 1998. Because phloretin does not inhibit INDY, this is further indication that INDY represents a new class of dicarboxylate transporters.

EXAMPLE 7

Effect of Indy on Fertility and Physical Activity

Figure 19:
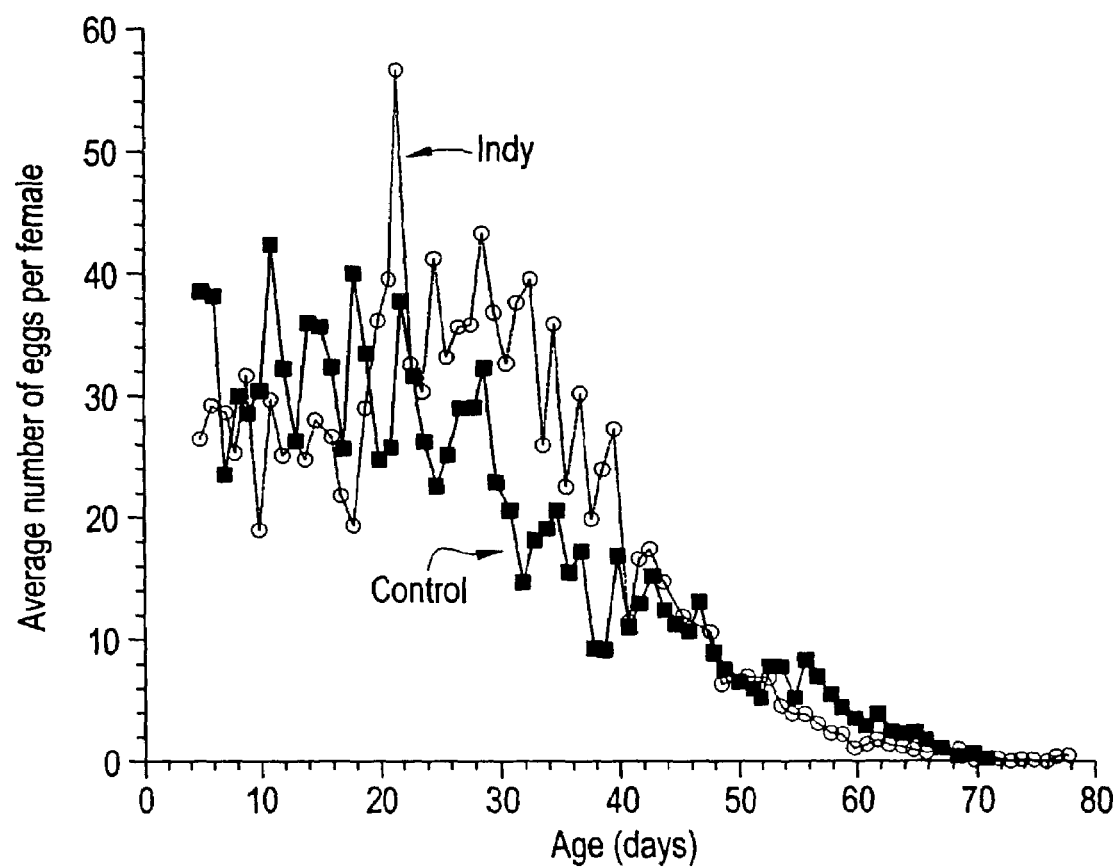
FIG. 19 shows the egg production of an Indy heterozygous female (open squares) compared to a normal female (closed squares) under high calorie conditions.

A decline in fertility or a reduction in physical activity can lead to an extension of life span in flies. Indy long-lived heterozygote males and females were compared to controls and found to be normal or superior in fertility and fecundity. Female fertility as measured by egg production is shown in FIG. 19. Qualitative observations of flight, courtship, feeding behavior and negative geotaxis revealed no significant differences between Indy long-lived males and females during early life. Differences occurred later in life when physical measures of behavior and locomotor function were maintained at high levels in Indy long-lived animals but not in normal-lived controls. For instance, one physiological milestone of aging in flies is the onset of female infertility. Indy heterozygous long-lived females continued to produce viable adult offspring 40% longer on average than did control flies (23.2 vs. 16.5 days). This was a true extension of the period of fertility and was not associated with a compensatory delay in fertility during early life, as seen in laboratory-selected long-lived lines. Indy long-lived females showed the same early peak of egg laying and fertility as control females but sustained the ability to produce larger numbers of offspring for a longer period of time. There was no alteration in the rate or timing of developmental events in Indy long-lived mutant animals, as in the *C. elegans* clock mutants. The time from egg to adult at 25° was the same as for normal controls (9 to 10 days). Studies on metabolic rate have also showed that Indy long-lived mutants have the same metabolic rate as controls suggesting that the increase in life-span in Indy mutants is not due to a slowing down of metabolic rate.

EXAMPLE 8

Relationship of Indy to Caloric Restriction

Figure 20:
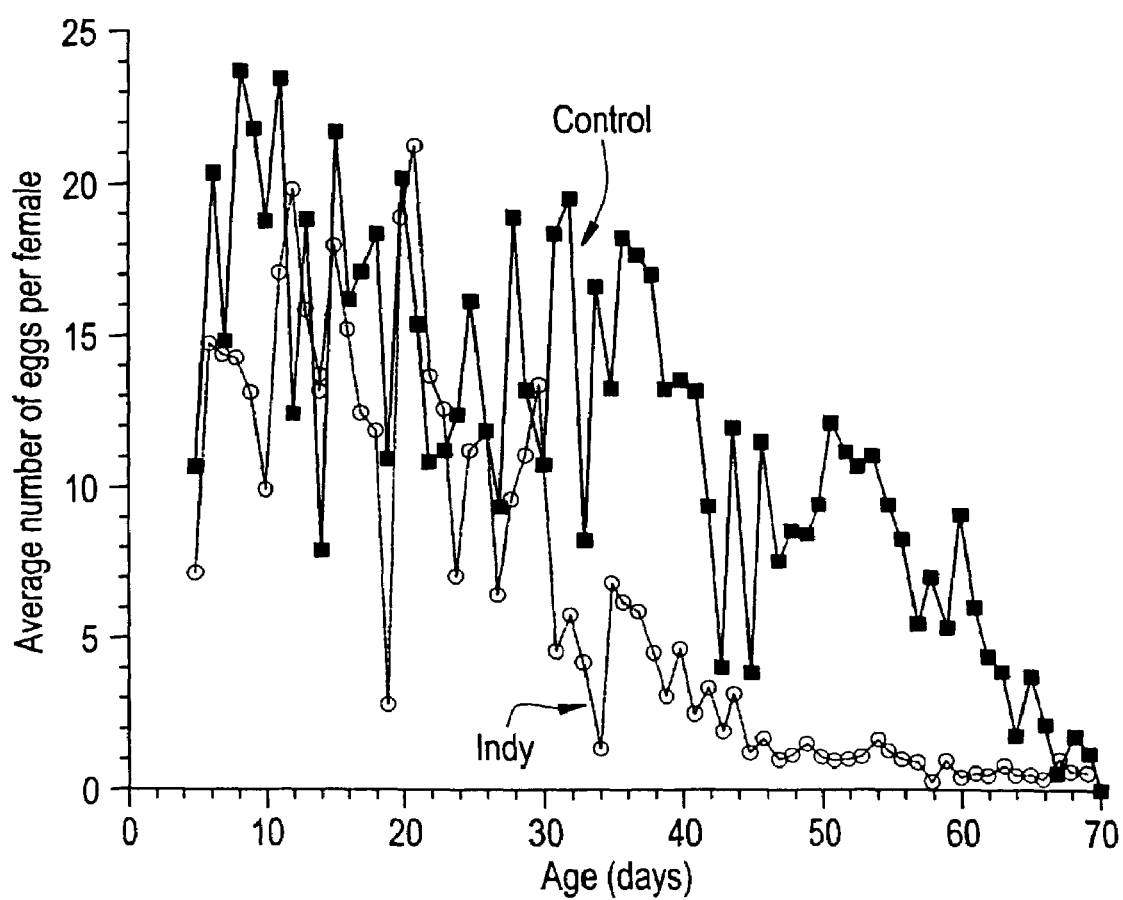
FIG. 20 shows the egg production of an Indy heterozygous female (open squares) compared to a normal female (closed squares) under low calorie conditions.

It has been proposed that Indy acts through a caloric restriction mechanism. Under normal high calorie feeding conditions, the egg production in Indy heterozygous females is comparable to normal females (FIG. 19). Under low calorie conditions, however, the egg production in Indy heterozygous females is significantly lower than that in normal females (FIG. 20). This result strongly suggests that Indy females are already calorically restricted and that by further restricting them through diet, a deleterious effect on fertility is observed.

Figure 21:
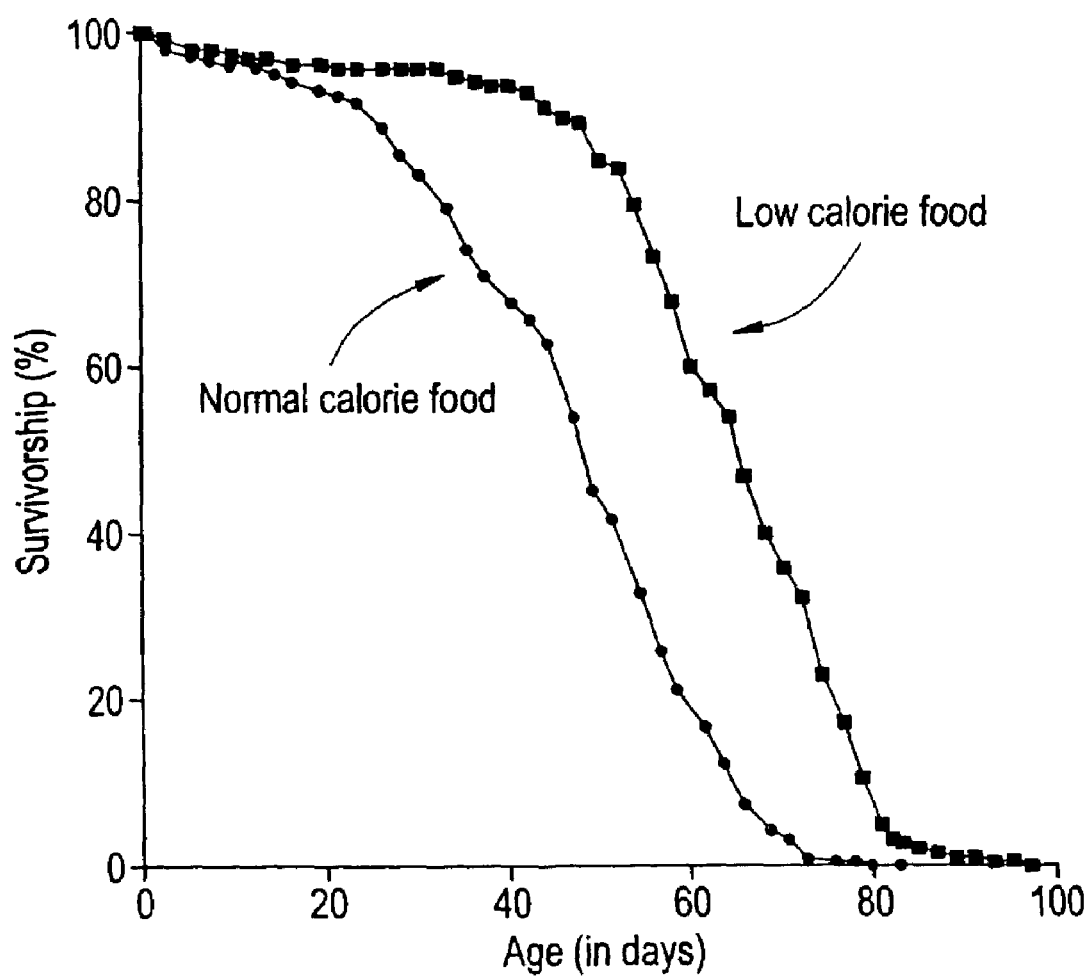
FIG. 21 shows survival curves for a normal fly fed normal calorie food (circles) or low calorie food (squares).
Figure 22:
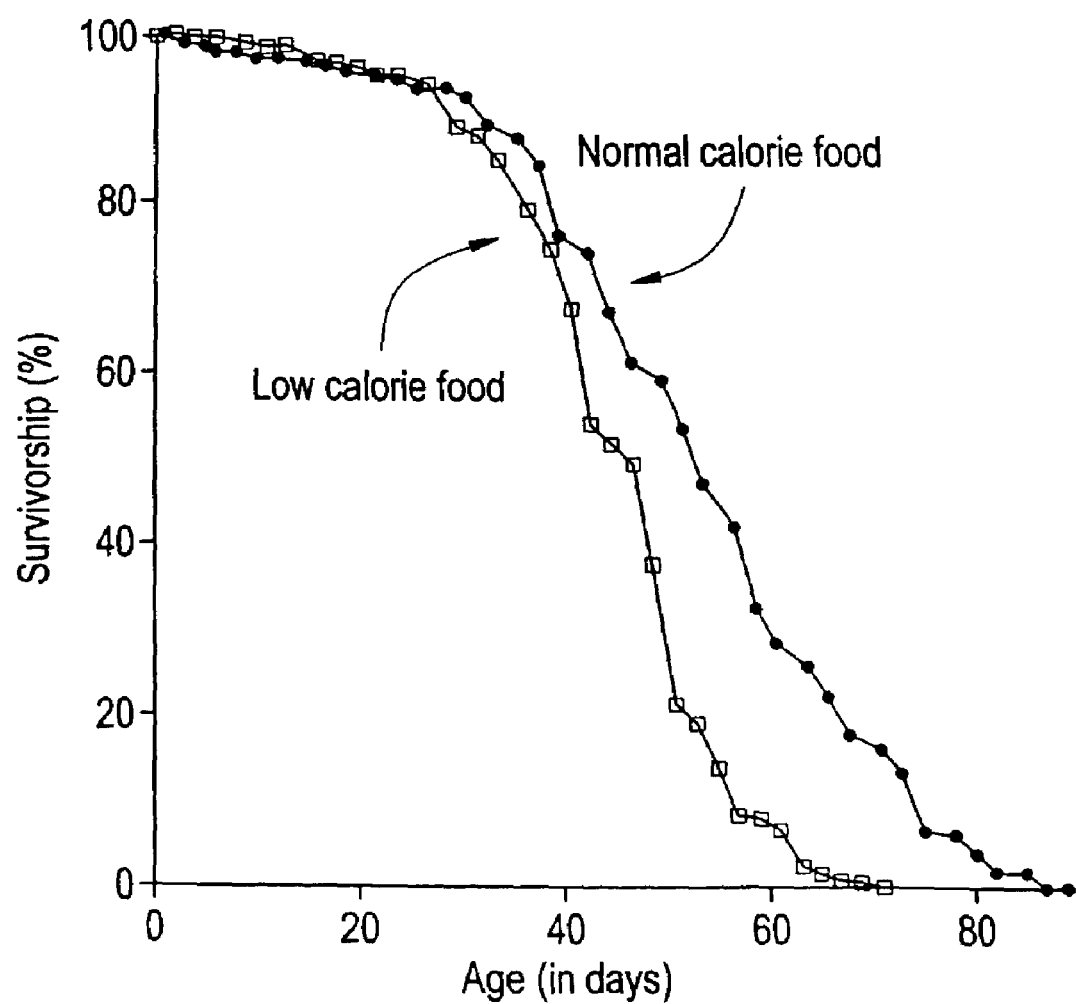
FIG. 22 shows survival curves for an Indy/Indy heterozygote fly fed normal calorie food (circles) or low calorie food (squares).

Further evidence for the relationship between Indy long-lived effects and caloric restriction is seen in the effect of caloric restriction on Indy mutant flies. In a normal fly, caloric restriction increases life-span (FIG. 21). In an Indy/ Indy mutant homozygous fly, caloric restriction decreases life-span (FIG. 22). This result suggests that further restriction of calories (such as through diet) in an Indy homozygous mutant fly decreases life span. It is thus believed that Indy mutants act by calorically restricting the flies and in heterozygotes (Indy/normal) flies the level of caloric restriction results in an increase in life-span.

EXAMPLE 9

Expression of Indy in Yeast

The Indy cDNA was ligated into pRS426-Gal using standard molecular biology techniques. The yeast cells were then transformed with the Indy-pRS426-Gal plasmid using standard protocols.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method to assess the inhibitory activity of a test substance on a polypeptide that comprises SEQ ID NO:2, the method comprising:
   contacting the polypeptide with the test substance in the presence of a carboxylate, wherein the polypeptide has been expressed by a cell; and
   detecting the amount of carboxylate transported by the polypeptide in the presence and absence of the test substance, wherein inhibition of transport in the presence as compared to the absence of the test substance indicates that the test substance is a cellular transporter inhibitor.

2. The method of claim 1 wherein the cell is a *Xenopus* oocyte.

3. A method to assess interaction of a test molecule with a transporter polypeptide, the method comprising:
   providing a transporter polypeptide that comprises SEQ ID NO:2,
   contacting the transporter polypeptide with a test molecule; and
   detecting binding of the test molecule to the transporter polypeptide, thereby assessing interaction of the test molecule with the transporter polypeptide.

4. The method of claim 3 wherein the method is used to screen a library of chemical compounds.

5. A method to assess interaction of a test molecule with a transporter polypeptide, the method comprising:
   providing a transporter polypeptide that comprises SEQ ID NO:2, wherein providing the transporter polypeptide comprises expressing the transporter polypeptide in a host cell such that the transporter polypeptide is present at the cell surface;
   contacting the transporter polypeptide with a test molecule; and
   detecting the transport activity in the presence and absence of the test molecule, wherein the step of detecting comprises contacting the transporter polypeptide with a carboxylate and assaying transport of the carboxylate, and wherein an alteration in the transport activity in the presence as compared to the absence of the test substance indicates that the test substance is a modulator of the transporter polypeptide.

6. The method of claim 5, wherein the carboxylate is selected from the group consisting of succinate, alpha-ketoglutarate, fumarate, and citrate.

7. The method of claim 6, wherein the carboxylate is succinate.

8. The method of claim 5, wherein the host cell is a *Xenopus* oocyte.

9. The method of claim 5, wherein the host cell is a mammalian cell.

10. The method of claim 3 or 5 wherein the test molecule is selected from the group consisting of antibodies, peptides, nucleic acid molecules, and small organic molecules.

11. The method of claim 5 wherein the method is used to screen a library of chemical compounds.

12. The method of claim 11 further comprising selecting one or more members from the library of chemical compounds that stimulate the transporter polypeptide.

13. The method of claim 11 further comprising selecting one or more members from the library of chemical compounds that inhibit the transporter polypeptide.

14. A method to assess a test molecule for ability to modulate expression of a transporter polypeptide, the method comprising:
   providing a cell that contains a nucleic acid encoding a transporter polypeptide that comprises SEQ ID NO:2;
   contacting a test molecule to the cell; and
   detecting expression of an mRNA that encodes the transporter polypeptide to determine whether the test molecule has the ability to modulate expression of the transporter polypeptide in the cell.

15. A method to assess transport activity by a transporter polypeptide, the method comprising:
   providing a cell that contains a nucleic acid encoding a transporter polypeptide that comprises SEQ ID NO:2;
   contacting a substrate of the transporter polypeptide to the cell; and
   detecting the substrate to determine transport of the substrate into the cell, thereby assessing transport activity of the transporter polypeptide.

16. The method of claim 15 wherein the contacting is in the presence of a test molecule.

17. The method of claim 15 wherein the substrate is a carboxylate.

18. The method of claim 17 wherein the substrate is succinate.

19. The method of claim 15 wherein the substrate is labeled.

20. The method of claim 15 wherein the transporter polypeptide is produced from a heterologous nucleic acid in the cell.

21. A method to assess the inhibitory activity of a test substance on a polypeptide that comprises SEQ ID NO:3, the method comprising:
   contacting the polypeptide which has been expressed by a cell with the test substance; and
   detecting the amount of carboxylate transported by the polypeptide in the presence and absence of the test substance by evaluating transport in the presence of a carboxylate, wherein inhibition of transport in the presence as compared to the absence of the test substance indicates that the test substance is a cellular transporter inhibitor.

* * * * *

SEQUENCE LISTING

```
<160> NUMBER OF SEQ ID NOS: 2

<210> SEQ ID NO 1
<211> LENGTH: 1719
<212> TYPE: DNA
<213> ORGANISM: Drosophila melanogaster
<220> FEATURE:
<221> NAME/KEY: CDS
<222> LOCATION: (1)..(1719)
<223> OTHER INFORMATION:
<300> PUBLICATION INFORMATION:
<301> AUTHORS: Blanka Rogina, Robert A. Reenan, Steven P. Nilsen and
      Stephen L. Helfand
<302> TITLE: Extended Life-Span Conferred by Cotransporter Gene
      Mutations in Drosophila
<303> JOURNAL: Science
<304> VOLUME: 290
<305> ISSUE: 5499
<306> PAGES: 2137-2140
<307> DATE: 2000-12-15
<309> DATABASE ENTRY DATE:
<313> RELEVANT RESIDUES: (1)..(1719)

<400> SEQUENCE: 1 atg gaa att gaa att ggc gaa caa ccc cag cct ccg gtg aag tgc tcc      48
Met Glu Ile Glu Ile Gly Glu Gln Pro Gln Pro Pro Val Lys Cys Ser
1               5                   10                  15 aac ttc ttc gct aac cac tgg aag gga ttg gtt gtg ttc ctg gtg ccg      96
Asn Phe Phe Ala Asn His Trp Lys Gly Leu Val Val Phe Leu Val Pro
            20                  25                  30 ctg cta tgt ctg cct gtt atg ctg cta aac gaa ggc gcc gaa ttt cgg     144
Leu Leu Cys Leu Pro Val Met Leu Leu Asn Glu Gly Ala Glu Phe Arg
        35                  40                  45 tgc atg tac ctc ctt ttg gta atg gcc ata ttt tgg gtt acg gaa gcc     192
Cys Met Tyr Leu Leu Leu Val Met Ala Ile Phe Trp Val Thr Glu Ala
    50                  55                  60 ttg cct ctc tat gtg acg tcc atg ata ccg att gtg gcc ttc cca ata     240
Leu Pro Leu Tyr Val Thr Ser Met Ile Pro Ile Val Ala Phe Pro Ile
65                  70                  75                  80 atg ggt ata atg agc tcg gat cag act tgc cgc ttg tac ttc aag gat     288
Met Gly Ile Met Ser Ser Asp Gln Thr Cys Arg Leu Tyr Phe Lys Asp
                85                  90                  95
```

-continued

| | |
|---|---|
| acg ctg gtg atg ttc atg ggc ggc att atg gtc gcc ctg gct gtg gag<br>Thr Leu Val Met Phe Met Gly Gly Ile Met Val Ala Leu Ala Val Glu<br>        100                     105                  110 | 336 |
| tac tgt aat cta cac aaa cgt ctt gcc ttg agg gta atc cag atc gtg<br>Tyr Cys Asn Leu His Lys Arg Leu Ala Leu Arg Val Ile Gln Ile Val<br>        115                     120                  125 | 384 |
| ggc tgc agt ccc cgc aga tta cac ttt ggc ctc atc atg gtt aca atg<br>Gly Cys Ser Pro Arg Arg Leu His Phe Gly Leu Ile Met Val Thr Met<br>130                     135                     140 | 432 |
| ttt ttg agc atg tgg att tcg aac gcc gcc tgt act gcc atg atg tgt<br>Phe Leu Ser Met Trp Ile Ser Asn Ala Ala Cys Thr Ala Met Met Cys<br>145                   150                     155                  160 | 480 |
| ccg att atc caa gcc gtg ctg gag gag ctg cag gct cag ggt gtc tgc<br>Pro Ile Ile Gln Ala Val Leu Glu Glu Leu Gln Ala Gln Gly Val Cys<br>                 165                     170                  175 | 528 |
| aaa atc aac cat gag cct caa tac caa atc gtt gga ggc aac aag aaa<br>Lys Ile Asn His Glu Pro Gln Tyr Gln Ile Val Gly Gly Asn Lys Lys<br>        180                     185                  190 | 576 |
| aac aac gag gat gag cca cca tac ccc acc aag atc act ctg tgc tac<br>Asn Asn Glu Asp Glu Pro Pro Tyr Pro Thr Lys Ile Thr Leu Cys Tyr<br>                 195                     200                  205 | 624 |
| tat ctg ggc att gcc tac gcc tcc tcg ctg ggt ggc tgt gga acc atc<br>Tyr Leu Gly Ile Ala Tyr Ala Ser Ser Leu Gly Gly Cys Gly Thr Ile<br>210                     215                     220 | 672 |
| atc gga act gcc acc aat ctt acc ttc aag ggc atc tac gag gct cgt<br>Ile Gly Thr Ala Thr Asn Leu Thr Phe Lys Gly Ile Tyr Glu Ala Arg<br>225                   230                     235                  240 | 720 |
| ttc aag aac tcc acc gaa cag atg gac ttc ccc acc ttc atg ttc tac<br>Phe Lys Asn Ser Thr Glu Gln Met Asp Phe Pro Thr Phe Met Phe Tyr<br>                 245                     250                  255 | 768 |
| tcg gtg cca tcc atg ttg gtc tac acc ttg ctg aca ttc gtg ttc ctg<br>Ser Val Pro Ser Met Leu Val Tyr Thr Leu Leu Thr Phe Val Phe Leu<br>        260                     265                  270 | 816 |
| caa tgg cac ttc atg ggt ctg tgg cgt ccc aag agc aag gag gca cag<br>Gln Trp His Phe Met Gly Leu Trp Arg Pro Lys Ser Lys Glu Ala Gln<br>                 275                     280                  285 | 864 |
| gaa gtc cag agg gga cga gag ggc gcc gat gtc gcc aaa aag gtt atc<br>Glu Val Gln Arg Gly Arg Glu Gly Ala Asp Val Ala Lys Lys Val Ile<br>290                     295                     300 | 912 |
| gat cag cgc tac aag gat ctg ggt ccc atg tcc att cac gag atc caa<br>Asp Gln Arg Tyr Lys Asp Leu Gly Pro Met Ser Ile His Glu Ile Gln<br>305                   310                     315                  320 | 960 |
| gtg atg att ctg ttc att ttt atg gtt gtg atg tac ttc acc cgc aag<br>Val Met Ile Leu Phe Ile Phe Met Val Val Met Tyr Phe Thr Arg Lys<br>                 325                     330                  335 | 1008 |
| ccc ggc atc ttt ttg gga tgg gcc gat ttg ctg aat tcc aag gac att<br>Pro Gly Ile Phe Leu Gly Trp Ala Asp Leu Leu Asn Ser Lys Asp Ile<br>                 340                     345                  350 | 1056 |
| cgt aac tct atg ccc act att ttt gtc gtc gtc atg tgc ttc atg ctg<br>Arg Asn Ser Met Pro Thr Ile Phe Val Val Val Met Cys Phe Met Leu<br>355                     360                     365 | 1104 |
| ccc gcc aat tat gct ttc cta cgc tac tgc acc aga cgc ggt ggt cca<br>Pro Ala Asn Tyr Ala Phe Leu Arg Tyr Cys Thr Arg Arg Gly Gly Pro<br>370                     375                     380 | 1152 |
| gtg ccc acg ggt ccc act cca tcg ctg atc acc tgg aag ttc atc cag<br>Val Pro Thr Gly Pro Thr Pro Ser Leu Ile Thr Trp Lys Phe Ile Gln<br>385                   390                     395                  400 | 1200 |
| acc aag gtg cca tgg ggt ctg gtg ttc ctg ctt ggc ggt ggc ttc gct<br>Thr Lys Val Pro Trp Gly Leu Val Phe Leu Leu Gly Gly Gly Phe Ala | 1248 |

-continued

```
                   405                 410                 415
ttg gcc gaa ggc agc aag cag agc ggc atg gcc aag ctg att ggc aat      1296
Leu Ala Glu Gly Ser Lys Gln Ser Gly Met Ala Lys Leu Ile Gly Asn
                420                 425                 430 gct ctg att gga ttg aag gtt ctg ccc aac tct gtc ctc tta ctg gtg      1344
Ala Leu Ile Gly Leu Lys Val Leu Pro Asn Ser Val Leu Leu Leu Val
            435                 440                 445 gtc atc ctg gtg gct gtg ttc ctg acc gcc ttc agc tcc aat gtg gcg      1392
Val Ile Leu Val Ala Val Phe Leu Thr Ala Phe Ser Ser Asn Val Ala
        450                 455                 460 att gcc aac att att att ccc gtt ctg gcc gag atg tcc ctg gcc att      1440
Ile Ala Asn Ile Ile Ile Pro Val Leu Ala Glu Met Ser Leu Ala Ile
465                 470                 475                 480 gag atc cat cct ctg tac ctg atc ctg ccc gct ggc ttg gcc tgc agt      1488
Glu Ile His Pro Leu Tyr Leu Ile Leu Pro Ala Gly Leu Ala Cys Ser
                485                 490                 495 atg gcc ttc cac ctg ccg gtt agt act ccg ccc aac gct ttg gtt gct      1536
Met Ala Phe His Leu Pro Val Ser Thr Pro Pro Asn Ala Leu Val Ala
                500                 505                 510 ggc tat gcc aac att agg acg aag gac atg gcc att gct gga atc ggt      1584
Gly Tyr Ala Asn Ile Arg Thr Lys Asp Met Ala Ile Ala Gly Ile Gly
            515                 520                 525 ccg acc atc att acc atc atc acc ctg ttt gtt ttc tgc caa acc tgg      1632
Pro Thr Ile Ile Thr Ile Ile Thr Leu Phe Val Phe Cys Gln Thr Trp
        530                 535                 540 ggc ctg gtt gtc tat ccg aac ctt aac tcg ttc ccc gaa tgg gct cag      1680
Gly Leu Val Val Tyr Pro Asn Leu Asn Ser Phe Pro Glu Trp Ala Gln
545                 550                 555                 560 att tat gcc gcg gca gca ctg gga aac aag acg cac tag                  1719
Ile Tyr Ala Ala Ala Ala Leu Gly Asn Lys Thr His
                565                 570

<210> SEQ ID NO 2
<211> LENGTH: 572
<212> TYPE: PRT
<213> ORGANISM: Drosophila melanogaster

<400> SEQUENCE: 2

Met Glu Ile Glu Ile Gly Glu Gln Pro Gln Pro Val Lys Cys Ser
1               5                   10                  15

Asn Phe Phe Ala Asn His Trp Lys Gly Leu Val Val Phe Leu Val Pro
                20                  25                  30

Leu Leu Cys Leu Pro Val Met Leu Leu Asn Glu Gly Ala Glu Phe Arg
            35                  40                  45

Cys Met Tyr Leu Leu Leu Val Met Ala Ile Phe Trp Val Thr Glu Ala
        50                  55                  60

Leu Pro Leu Tyr Val Thr Ser Met Ile Pro Ile Val Ala Phe Pro Ile
65                  70                  75                  80

Met Gly Ile Met Ser Ser Asp Gln Thr Cys Arg Leu Tyr Phe Lys Asp
                85                  90                  95

Thr Leu Val Met Phe Met Gly Gly Ile Met Val Ala Leu Ala Val Glu
            100                 105                 110

Tyr Cys Asn Leu His Lys Arg Leu Ala Leu Arg Val Ile Gln Ile Val
        115                 120                 125

Gly Cys Ser Pro Arg Arg Leu His Phe Gly Leu Ile Met Val Thr Met
    130                 135                 140

Phe Leu Ser Met Trp Ile Ser Asn Ala Ala Cys Thr Ala Met Met Cys
145                 150                 155                 160
```

```
Pro Ile Ile Gln Ala Val Leu Glu Glu Leu Gln Ala Gln Gly Val Cys
            165                 170                 175

Lys Ile Asn His Glu Pro Gln Tyr Gln Ile Val Gly Gly Asn Lys Lys
            180                 185                 190

Asn Asn Glu Asp Glu Pro Pro Tyr Pro Thr Lys Ile Thr Leu Cys Tyr
            195                 200                 205

Tyr Leu Gly Ile Ala Tyr Ala Ser Ser Leu Gly Gly Cys Gly Thr Ile
210                 215                 220

Ile Gly Thr Ala Thr Asn Leu Thr Phe Lys Gly Ile Tyr Glu Ala Arg
225                 230                 235                 240

Phe Lys Asn Ser Thr Glu Gln Met Asp Phe Pro Thr Phe Met Phe Tyr
            245                 250                 255

Ser Val Pro Ser Met Leu Val Tyr Thr Leu Leu Thr Phe Val Phe Leu
            260                 265                 270

Gln Trp His Phe Met Gly Leu Trp Arg Pro Lys Ser Lys Glu Ala Gln
            275                 280                 285

Glu Val Gln Arg Gly Arg Glu Gly Ala Asp Val Ala Lys Lys Val Ile
290                 295                 300

Asp Gln Arg Tyr Lys Asp Leu Gly Pro Met Ser Ile His Glu Ile Gln
305                 310                 315                 320

Val Met Ile Leu Phe Ile Phe Met Val Val Met Tyr Phe Thr Arg Lys
            325                 330                 335

Pro Gly Ile Phe Leu Gly Trp Ala Asp Leu Leu Asn Ser Lys Asp Ile
            340                 345                 350

Arg Asn Ser Met Pro Thr Ile Phe Val Val Met Cys Phe Met Leu
            355                 360                 365

Pro Ala Asn Tyr Ala Phe Leu Arg Tyr Cys Thr Arg Arg Gly Gly Pro
            370                 375                 380

Val Pro Thr Gly Pro Thr Pro Ser Leu Ile Thr Trp Lys Phe Ile Gln
385                 390                 395                 400

Thr Lys Val Pro Trp Gly Leu Val Phe Leu Leu Gly Gly Gly Phe Ala
            405                 410                 415

Leu Ala Glu Gly Ser Lys Gln Ser Gly Met Ala Lys Leu Ile Gly Asn
            420                 425                 430

Ala Leu Ile Gly Leu Lys Val Leu Pro Asn Ser Val Leu Leu Leu Val
            435                 440                 445

Val Ile Leu Val Ala Val Phe Leu Thr Ala Phe Ser Ser Asn Val Ala
450                 455                 460

Ile Ala Asn Ile Ile Pro Val Leu Ala Glu Met Ser Leu Ala Ile
465                 470                 475                 480

Glu Ile His Pro Leu Tyr Leu Ile Leu Pro Ala Gly Leu Ala Cys Ser
            485                 490                 495

Met Ala Phe His Leu Pro Val Ser Thr Pro Pro Asn Ala Leu Val Ala
            500                 505                 510

Gly Tyr Ala Asn Ile Arg Thr Lys Asp Met Ala Ile Ala Gly Ile Gly
            515                 520                 525

Pro Thr Ile Ile Thr Ile Ile Thr Leu Phe Val Phe Cys Gln Thr Trp
            530                 535                 540

Gly Leu Val Val Tyr Pro Asn Leu Asn Ser Phe Pro Glu Trp Ala Gln
545                 550                 555                 560

Ile Tyr Ala Ala Ala Ala Leu Gly Asn Lys Thr His
            565                 570
```